United States Patent [19]

Berger et al.

[11] Patent Number: 5,015,639
[45] Date of Patent: May 14, 1991

[54] SUBSTITUTED BENZAZEPINES, THEIR PREPARATION AND PHARMACEUTICAL COMPOSITIONS CONTAINING THEM

[75] Inventors: Joel G. Berger, Cedar Grove; Wei K. Chang, Livingston, both of N.J.; Marjorie Peters, Saint Simons Island, Ga.

[73] Assignee: Schering Corporation, Kenilworth, N.J.

[21] Appl. No.: 322,801

[22] Filed: Mar. 13, 1989

Related U.S. Application Data

[63] Continuation-in-part of PCT US88/00899, Mar. 27, 1987, abandoned.

[51] Int. Cl.$^5$ .................. A61K 31/55; A61K 31/495; C07D 403/02; C07D 223/16
[52] U.S. Cl. .................. 514/213; 540/594; 540/595
[58] Field of Search .................. 540/594; 514/213

[56] References Cited

U.S. PATENT DOCUMENTS

| 3,393,192 | 7/1968 | Walter et al. ............ 260/239 R |
| 3,609,138 | 9/1971 | Mull et al. ................ 260/239 |
| 4,011,319 | 3/1977 | Kaiser et al. ............. 424/244 |
| 4,187,314 | 2/1980 | Holden et al. ........... 260/340.3 |
| 4,197,297 | 4/1980 | Weinstock ................ 540/595 |
| 4,265,889 | 5/1981 | Brush et al. ............. 540/595 |
| 4,284,555 | 8/1981 | Gold et al. .............. 260/239 BB |
| 4,477,378 | 10/1984 | Gold et al. ............. 260/239 BB |

FOREIGN PATENT DOCUMENTS

| 0005299 | 11/1979 | European Pat. Off. ........... 540/595 |
| 0200455 | 11/1986 | European Pat. Off. . |
| 0096838 | 12/1986 | European Pat. Off. . |
| 1934150 | 7/1979 | Fed. Rep. of Germany . |
| 1118688 | 7/1968 | United Kingdom . |
| 1221324 | 2/1971 | United Kingdom . |
| 1268243 | 3/1972 | United Kingdom . |

OTHER PUBLICATIONS

J. Richard Heys—High-Performance Liquid Chromatographic Studies of pH Dependence in the Isotopic Fractionation of Deuterated Benzazepines, J. Chromatography, 407, pp. 37–47 (1987).

*Primary Examiner*—David B. Springer
*Attorney, Agent, or Firm*—Warrick E. Lee, Jr.; James R. Nelson; Matthew Boxer

[57] ABSTRACT

Disclosed herein are novel 1-substituted-2,3,4,5-tetrahydro-1H-3-benzazepines of the general formula I:

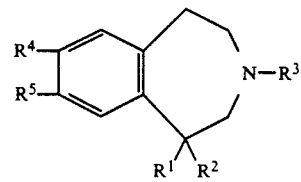

wherein $R^1$, $R^2$, $R^3$, $R^4$ and $R^5$ are specified substituents. $R^1$ is preferably —$X^6$, —$CHR^7R^8$, cycloalkyl, cycloalkenyl,

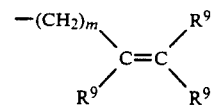

or pyrrolyl where m is 1, $R^6$ represents =H, phenyl, substituted phenyl, aralkyl, alkyl, cycloalkyl, haloalkyl or alkoxyalkyl, $R^7$ represents H or alkyl preferably H, $R^8$ represents cycloalkyl, cycloalkenyl, haloalkyl, alkoxyalkyl, alkenyl or alkynyl and $R^9$ represents alkyl, aloxy or alkoxyalkyl.

$R^2$ preferably represents —H and $R^3$—$CH_3$, and $R^4$ is preferably halogen and $R^5$ is preferably OH, OCO.$R^9$ or —$O(CR^7)_2.OCO.R^{13}$ where $R^7$ represents hydrogen, $R^9$ is as defined above and $R^{13}$ represents alkyl. The compounds of the formula I are indicated as being useful in the treatment of psychoses, depression and pain. Also disclosed are process for the preparation of the novel compounds as well as pharmaceutical compositions comprising them.

11 Claims, No Drawings

SUBSTITUTED BENZAZEPINES, THEIR PREPARATION AND PHARMACEUTICAL COMPOSITIONS CONTAINING THEM

The present application is a continuation of copending International Application No. PCT/US 88/00899, filed Mar. 24, 1988 and designating the United States, the benefit of which is claimed pursuant to the provisions of 35 U.S.C. SS120, 363 and 365(c), which PCT application is in turn a continuation-in-part of copending U.S. application Ser. No. 032,135, filed Mar. 27, 1987, abandoned.

BACKGROUND OF THE INVENTION

This invention relates to novel 1- or 5-substituted-2,3,4,5-tetrahydro-1H-3-benzazepines, their preparation and to pharmaceutical compositions containing them. The compounds have valuable pharmaceutical properties in the treatment of psychoses, depression, pain and hypertension.

Substituted 1-phenyl-2,3,4,5-tetrahydro-1H-3-benzazepines have been described in the art. For example, see U.S. Pat. Nos. 3,393,192, 3,609,138, 4,011,319, 4,284,555 and 4,477,378 as well as British Patent 1,118,688. The activities discussed for the compounds disclosed in these patents include antibacterial effects, central nervous system effects and hypotensive effects.

Weinstock et al. in *Drugs of the Future*, Vol. 10, No. 8, pp 645–697 (1985) discuss the profound effect that 1-phenyl substituents have on the dopaminergic activity of certain types of benzazepines. See Table II on page 686.

European Patent Application No. 83105610.6 (Publication No. 0 096 838) discloses certain 1-aryloxy substituted 2,3,4,5-tetrahydro-3-benzazepines having H and/or alkoxy substituents in the 7- and 8-positions thereof. These compounds are disclosed as having utility in the treatment of depression.

SUMMARY OF THE INVENTION

It has now surprisingly been found that certain novel benzazepines lacking such a 1-phenyl substituent provide good anti-dopaminergic activity, in particular, showing surprising selectivity for the D-1 subclassification of dopaminergic receptors. Accordingly, in one of its aspects, the present invention provides novel benzazepines of the structural formula I:

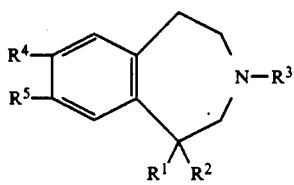

and the pharmaceutically acceptable salts thereof, wherein:

$R^1$ represents $-XR^6$, $-CHR^7R^8$, cycloalkyl, cycloalkenyl, $-H$, $-CN$, $-(CO)OR^9$, $-O(CO)R^9$, $-O(CO)N(R^9)_2$, $-C\equiv CR^9$, $-(CO)N(R^9)_2$, $$-(CH_2)_m\underset{R^9}{\overset{R^9}{C}}=C\underset{R^9}{\overset{R^9}{}}, \quad -Y\underset{(CH_2)_q}{\overset{(CH_2)_p}{}}Z,$$

imidazolyl or pyrrolyl;

$R^2$ represents $-H$ (provided that $R^1$ does not represent H), $-OH$ (provided that $R^1$ does not represent $-OH$ or $-SH$), or alkoxy;

in addition, $R^1$ and $R^2$ may together represent a carbonyl oxygen, a group =CH-aryl, or a group of the formula $$\underset{B}{\overset{W\diagup\diagdown W}{\diagdown\diagup}}$$

wherein B represents alkanediyl and W represents $-O-$, $-S-$, or $-CH_2-$;

$R^3$ represents H, alkyl, allyl or cyclopropylmethyl;

$R^4$ represents H, halo, alkyl, haloalkyl or alkoxy;

$R^5$ represents $-OR^{10}$, $-N(R^9)_2$ or $-O.C(R^7)_2.OCOR^{13}$;

$R^6$ represents $-H$, aryl, heteroaryl, naphthyl, aralkyl, heteroarylalkyl, alkyl, cycloalkyl, cycloalkenyl, haloalkyl, alkenyl, alkynyl, cycloalkylalkyl, cycloalkenylalkyl, alkoxyalkyl or $-(CH_2)_nR^{11}$;

$R^7$ represents $-H$ or alkyl;

$R^8$ represents cycloalkyl, cycloalkenyl, cycloalkylalkyl, cycloalkenylalkyl, aralkenyl, aralkynyl, heteroaryl, heteroarylalkyl, alkenyl, alkynyl, haloalkyl, alkoxyalkyl or $-(CH_2)_nR^{12}$;

each $R^9$ independently represents H, alkyl, alkoxy, alkoxyalkyl, aralkyl or aryl;

$R^{10}$ represents H, $-COR^9$ or $-CON(R^9)_2$;

$R^{11}$ represents $-(CO)OR^9$, $-COR^9$, $-(CO)N(R^9)_2$, $-CN$, $-O(CO)N(R^9)_2$, $-O(CO)R^9$, $-N(R^9)_2$, $-OR^9$ or $-SR^9$, provided that $R^{11}$ is not $-N(R^9)_2$, $-OR^9$ or $-SR^9$ when n is 1;

$R^{12}$ represents $-(CO)OR^9$, $-COR^9$, $-(CO)N(R^9)_2$, $-CN$, $-O(CO)N(R^9)_2$, $-O(CO)R^9$, $-N(R^9)_2$, $-OR^9$ OR $-SR^9$;

$R^{13}$ represents alkyl, aralkyl or aryl;

X represents $-O-$, $-S-$, or $-N(R^9)-$;

m represents 0 or 1;

n represents an integer of from 1 to 4;

Y represents N or CH;

Z represents $CH_2$ (if Y does not represent CH) or $NR^9$; and p and q each independently represent integers of from 1 to 3 such that the sum of p plus q is from 1 to 5 and p and q do not both represent 1 when Y is N and Z is $NR^9$.

When utilized herein and in the appended claims, the following terms, unless otherwise specified, have the following scope:

halo (including the halo of haloalkyl)—represents fluoro, chloro, bromo or iodo;

alkyl (including the alkyl portions of cycloalkylalkyl, cycloalkenylalkyl, heteroarylalkyl, alkoxy, alkoxyalkyl, etc.)—represents straight or branched carbon chains having 1 to 6 carbon atoms;

cycloalkyl (including the cycloalkyl portion of cycloalkylalkyl)—represents a saturated carbocyclic ring containing from 3 to 8 carbon atoms;

cycloalkenyl (including the cycloalkenyl portion of cycloalkenylalkyl)—represents a carbocyclic ring containing a carbon-carbon double bond and having 5 to 8 carbon atoms;

alkenyl (including the alkenyl portions of aralkenyl-)—represents straight or branched carbon chains having at least one carbon-carbon double bond and containing from 2 to 6 carbon atoms;

alkynyl (including the alkynyl portion of aralkynyl-)—represents straight or branched carbon chains having at least one carbon-carbon triple bond and containing from 2 to 6 carbon atoms;

aryl (including the aryl moiety in aralkyl, aralkenyl and aralkynyl)—represents unsubstituted phenyl or substituted phenyl;

substituted phenyl—represents phenyl mono- or di-substituted by alkyl, hydroxy, alkoxy, alkylthio, halo, trifluoromethyl or combinations thereof;

carbonyl oxygen—represents a group =O;

haloalkyl - represents an alkyl group as defined above containing from 1 to 5 halo groups, (preferably chloro or fluoro) replacing some or all of the hydrogens thereon depending on the sites of possible halogenation, e.g., $CF_3$, —$CH_2Cl$, etc.;

alkanediyl—represents a divalent, straight or branched hydrocarbon chain having from 1 to 6 carbon atoms, the two available bonds being from the same or different carbon atoms thereof, e.g., methylene, ethylene, ethylidene, —$CH_2CH_2CH_2$—,

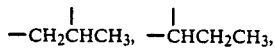

etc.; and heteroaryl (including the heteroaryl portion of heteroarylalkyl)—represents aromatic heterocyclic groups having at least one O, S and/or N interrupting the carbocyclic structure and having a sufficient number of delocalized pi electrons to provide aromatic character, with the aromatic heterocyclic groups preferably containing from 2 to 14 carbon atoms, e.g., 2-, 3- or 4-pyridyl, 2- or 3-furyl, 2- or 3-thienyl, 2-, 4- or 5-thiazolyl, 1-, 2- or 4-imidazolyl, 2-, 4-, 5- or 6-pyrimidinyl, 2- or 3-pyrazinyl, 3- or 4-pyridazinyl, 3-, 5- or 6-[1-, 2-, 4-triazinyl], 2-, 3-, 4-, 5-, 6- or 7-benzofuranyl, 2-, 3-, 4-, 5-, 6- or 7-indolyl, 1-, 3-, 4- or 5-pyrazolyl, 2-, 4- or 5-oxazolyl, etc., with all available substitutable carbon or nitrogen atoms thereof being intended as a possible point of attachment to the benzazepine ring system.

In a preferred embodiment of the invention, $R^1$ represents —$XR^6$, —$CHR^7R^8$, cycloalkyl or cycloalkenyl, wherein $R^6$ represents —H, phenyl, substituted phenyl, aralkyl, alkyl, haloalkyl or alkoxyalkyl, X represents —O— or —S—, $R^7$ represents H or alkyl, and $R^8$ represents cycloalkyl, cycloalkenyl, haloalkyl or alkoxyalkyl. Especially preferred values of $R^1$ are cycloalkyl and cycloalkenyl, in particular cyclohexyl and cyclohexenyl. Where $R^1$ is $XR^6$, preferred values for $R^6$ are alkyl, in particular methyl and ethyl and cycloalkyl, in particular cyclohexyl, and preferred values for X are —O— and —S—.

In a further preferred embodiment of the invention, $R^1$ represents

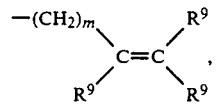

wherein m is 1 and $R^9$ is hydrogen or alkyl. In another further preferred embodiment of the invention $R^1$ is 1-pyrrolyl.

For $R^2$, a preferred value is —H and for $R^3$ a preferred value is —$CH_3$. $R^4$ is preferably halogen, in particular chloro, and $R^5$ is preferably —OH, —O.CO.$R^9$ or —OC($R^7$)$_2$OCOR$^{13}$ where $R^9$ represents alkyl, alkoxy or alkoxyalkyl, $R^7$ represents hydrogen and $R^{13}$ represents alkyl.

Preferred compounds of the general formula I include:

8-chloro-5-methoxy-3-methyl-2,3,4,5-tetrahydro-1H-3-benzazepine-7-ol, 8-chloro-5-ethoxy-3-methyl-2,3,4,5-tetrahydro-1H-3-benzazepine-7-ol, 8-chloro-5-ethylthio-3-methyl-2,3,4,5-tetrahydro-1H-3-benzazepine-7-ol, 8-chloro-3-methyl-5-phenoxy-2,3,4,5-tetrahydro-1H-3-benzazepin-7-ol, 8-chloro-3-methyl-5-phenylthio-2,3,4,5-tetrahydro-1H-3-benzazepin-7-ol, 7-chloro-8-dimethylcarbamoyl-1-ethoxy-methyl-2,3,4,5-tetrahydro-1H-3-benzazepine, 8-chloro-3-methyl-5-(1-piperidinyl)-2,3,4,5-tetrahydro-1H-3-benzazepine-7-ol, 8-chloro-5-cyclohexyl-3-methyl-2,3,4,5-tetrahydro-1H-3-benzazepine-7-ol, 8-chloro-5-cyclohexyloxy-3-methyl-2,3,4,5-tetrahydro-1H-3-benzazepine-7-ol, 8-chloro-5-(N,N-dimethylaminopropyl)-3-methyl-2,3,4,5-tetrahydro-1H-3-benzazepine-7-ol, 8-chloro-5-(2-cyclohexenyl)-3-methyl-2,3,4,5-tetrahydro-1H-3-benzazepine-7-ol, 8-chloro-5-allyl-3-methyl-2,3,4,5-tetrahydro-1H-3-benzazepine-7-ol, 8-chloro-5-(2,2,2-trifluoroethoxy)-3-methyl-2,3,4,5-tetrahydro-1H-3-benzazepine-7-ol, 8-chloro-5-benzyloxy-3-methyl-2,3,4,5-tetrahydro-1H-3-benzazepine-7-ol, 8-chloro-5-(phenethyloxy)-3-methyl-2,3,4,5-tetrahydro-1H-3-benzazepine-7-ol, 8-chloro-5-(1-pyrrolyl)-3-methyl-2,3,4,5-tetrahydro-1H-3-benzazepine-7-ol, 8-chloro-7-hydroxy-3-methyl-2,3,4,5-tetrahydrospiro[1H-3-benzazepine-5,5'-cyclopentane], 8-chloro-7-(ethoxy-formyloxy)-5-cyclohexyl-3-methyl-2,3,4,5-tetrahydro-1H-3-benzazepine, 8-chloro-7-(isopropyl-formyloxy)-5-allyl-3-methyl-2,3,4,5-tetrahydro-1H-3-benzazepine, 8-chloro-7-(methoxy-acetoxy)-5-allyl-3-methyl-2,3,4,5-tetrahydro-1H-3-benzazepine, 8-chloro-7-acetoxy-5-(3-methyl-2-butenyl)-3-methyl-2,3,4,5-tetrahydro-1H-3-benzazepine, 8-chloro-7-(t-butyryloxy-methoxy)-5-allyl-3-methyl-2,3,4,5-tetrahydro-1H-3-benzazepine, and the pharmaceutically acceptable salts of the foregoing.

In another of its aspects, the present invention provides a process for the preparation of a compound of the formula I which process comprises a process selected from the following processes A to E:

A: reduction of a carbonyl compound of the general formula:

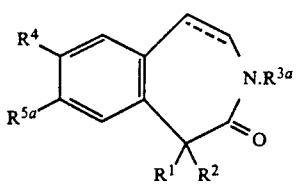

B: reduction of an ester of the general formula:

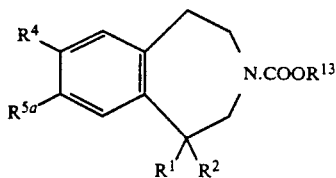

C: reduction at the double bond of a salt of the general formula:

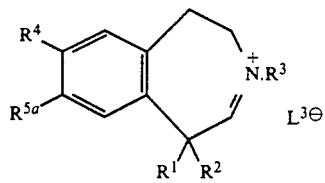

D: intramolecular condensation of a compound of the general formula:

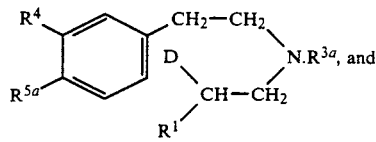

with elimination of HD and formation of the azepine ring,

E: reduction at the olefinic double bond of a compound of the general formula:

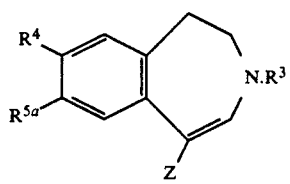

wherein in the foregoing formulae the dotted line in the azepine ring represents a facultative double bond, $R^1$, $R^2$, $R^3$, $R^4$ and $R^{13}$ are as defined for formula I, $R^{3a}$ is $R^3$ or $COOR^{13}$, $R^{5a}$ is $R^5$ as defined for formula I or is alkoxy, $L^3$ is an anion, preferably an anion derived from a halo acid or a sulfonic acid, D is a reactive group capable of being eliminated as DH with formation of the azepine ring, and Z is $R^1$ or $R^2$, said process being followed if desired by one or more of the following facultative steps:

(i) removal of any protecting group present at the nitrogen atom,
(ii) alkylation at the nitrogen atom wherein $R^3$ is hydrogen to introduce $R^3$ representing alkyl, allyl or cyclopropyl,
(iii) etherification or thioetherification of $R^1$ wherein $R^1$ is —OH and $R^2$ is —H to give a corresponding ether or thiol,
(iv) esterification of $R^5$ wherein $R^5$ is —OH,
(v) halogenation of $R^4$ where $R^4$ is —H,
(vi) hydroxymethylation of $R^4$ wherein $R^4$ is —H, followed by reduction of the so-introduced hydroxymethyl group to methyl, and before or after said facultative step or steps, dealkylation of $R^{5a}$ where $R^{5a}$ is alkoxy, the so-obtained compound of the formula I being isolated in free form or in the form of a pharmaceutically acceptable salt.

The present invention also includes intermediates useful in the preparation of the compounds of formula I, i.e., intermediates of formula II

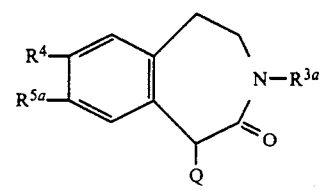

wherein $R^{3a}$ represents $R^3$ as defined above or —$COOR^{14}$ wherein $R^{14}$ is alkyl, aryl, aralkyl or haloalkyl; $R^4$ is as defined above; $R^{5a}$ represents $R^5$ as defined above or alkoxy; and Q represents H, halo or —$SO_2R''$ wherein $R''$ is $CH_3$, $CF_3$, phenyl or tolyl. Q preferably represents chloro or bromo. A preferred intermediate is of the formula IIa

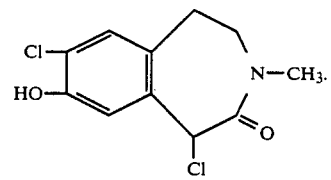

The compounds of formula I possess analgesic, anticholinergic, antiaggressive and general tranquilizing properties. The invention therefore includes pharmaceutical compositions comprising a compound of formula I in combination with a pharmaceutically acceptable carrier and methods for treating mental disorders including psychoses, schizophrenia or depression in a mammal, or for the control of pain or anxiety in a mammal by administering an effective amount of a compound of formula I to the affected mammals.

DETAILED DESCRIPTION OF THE INVENTION

Certain compounds of the invention, e.g., where $R^1$ and $R^2$ are different, may exist in isomeric forms. The invention contemplates all such isomers both in pure form and in admixture, including racemic mixtures.

Compounds of formula I can exist in unsolvated as well as solvated forms, including hydrated forms, e.g., hemihydrate. In general, the solvated forms, with pharmaceutically acceptable solvents such as water, ethanol and the like are equivalent to the unsolvated forms for purposes of this invention.

The compounds of formula I may form pharmaceutically acceptable salts with organic and inorganic acids. Examples of suitable acids for salt formation are hydrochloric, sulfuric, phosphoric, acetic, citric, malonic, salicylic, malic, fumaric, succinic, ascorbic, maleic, methanesulfonic and other mineral and carboxylic acids well known to those in the art. The salts are prepared by contacting the free base form with a sufficient amount of the desired acid to produce a salt in the conventional manner. The free base forms may be regenerated by treating the salt with a suitable dilute aqueous base solution such as dilute aqueous sodium hydroxide, potassium carbonate, ammonia and sodium bicarbonate. The free base forms differ from their respective salt forms somewhat in certain physical properties, such as solubility in polar solvents, but the salts are otherwise equivalent to their respective free base forms for purposes of the invention.

The compounds of formula I above may be prepared of the methods A-E described below:

A. A compound of formula III may be reacted with a suitable reducing agent to reduce the carbonyl oxygen:

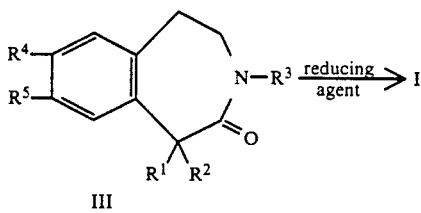

III

Suitable reducing agents include BH$_3$/THF, LiAlH$_4$, NaBH$_4$/ pyridine, NaAlH$_2$(OCH$_2$CH$_2$OC$_2$H$_5$)$_2$, etc. The reaction may be performed at any suitable temperature, e.g. from about 0° C. to about 120° C., and may be performed in an inert solvent such as THF, ether, etc.

The compounds of formula III may be prepared by the processes described below:

For example, a compound of formula IV below may be reacted with a compound of formula V to form a compound of formula VI:

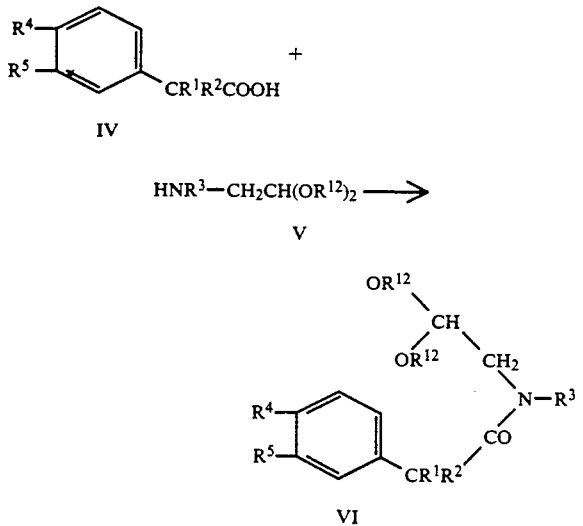

VI wherein R$^{12}$ is an alkyl group such methyl or ethyl. This reaction may be performed at any suitable temperature, e.g., from about 0° C. to about 50° C. Usually an inert solvent such as DMF, CH$_2$Cl$_2$, etc., is employed but the reaction may also be run neat. The reaction is run in the presence of coupling agents or dehydration agents such as dicyclohexylcarbodiimide, N-ethyl—N'-(dimethylamino)ethylcarbodiimide, etc.

Alternatively, the compounds of formula VI can be made by reacting the compounds of formula IV with, for example, SOCl$_2$ or (COCl)$_2$ to yield the acid chloride of formula IVa

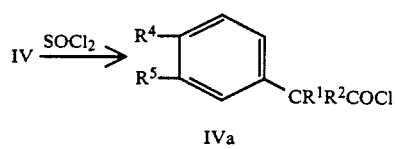

IVa which is then reacted with a compound of formula V. In this reaction, there is no need for a coupling agent.

Compounds of formula IV are either known or may be prepared by techniques conventional in the art. The acetals of formula V are likewise known or easily prepared by conventional techniques. See U.S. Pat. No. 4,490,369.

The acetal of formula VI is reacted with a strong acid such as CF$_3$SO$_3$H, HCl, etc. to produce a compound of formula VII:

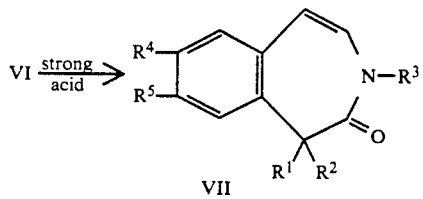

VII

This reaction may be run neat, i.e., with the acid as the solvent, or in the presence of a solvent such as acetic acid. Any suitable temperature may be employed, e.g., from about 0° C. to about 50° C.

The compounds of formula VII are then reduced to a compound of formula III by employing a suitable hydrogenation agent which will reduce the olefinic bond of formula VII without reducing the carbonyl thereof, e.g., H$_2$/PtO$_2$, H$_2$/Pd-C, etc.:

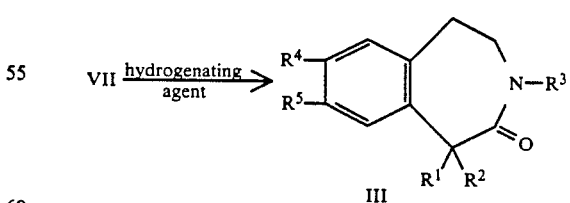

III

Alternatively, the compounds of formula III may be prepared by a sequence of steps starting with reacting a compound of formula IVb with a compound of formula V to produce a compound of formula VIa, which is then reacted with a strong acid and then a reducing agent to form a compounds of formulas VIIa and VIII, as shown below:

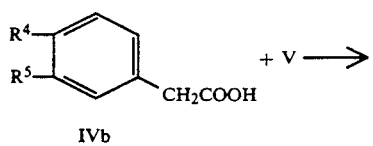

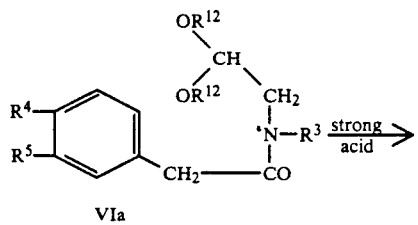

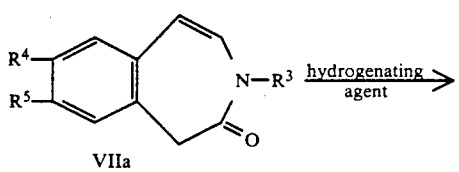

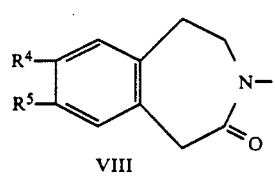

wherein $R^{12}$ is as defined above. These reactions may be performed under the conditions described above for the respective reaction.

The compound of formula VIII is reacted with a halogenating agent such as $SO_2Y_2$, e.g., $SO_2Cl_2$, $SO_2Br_2$, etc., to produce a compound of formula IX:

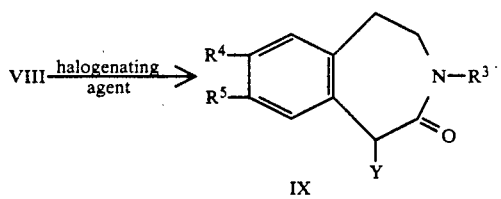

This reaction may be run at any suitable temperature and is usually performed in an inert solvent such as $CH_2Cl_2$, $CHCl_3$, etc.

The Y group in the compound of formula IX can be hydrolyzed to an OH group which may then be reacted with an appropriate sulfonyl halide or anhydride (such as tolylsulfonyl chloride or methanesulfonyl chloride) to provide other intermediates of formula II above.

The compound of formula IX or the sulfonyl derivatives thereof as described in the preceding paragraph may be reacted with a suitable nucleophile (nu) wherein Y is displaced to prepare a compound of formula X:

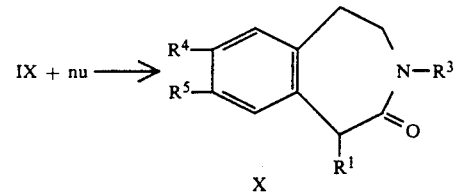

The nucleophile is the precursor of the group $R^1$ and can be, for example, an alkanol, primary or secondary amine, a thiol, sodioethylmalonate, cyanide, etc.

If it is desired that $R^2$ be other than hydrogen, the compound of formula X may be reacted with a suitable halogenating agent as described above to form a compound of formula XI:

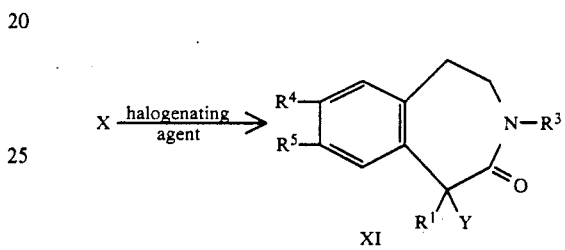

The compound of formula XI is then reacted with a nucleophile (nu) which is the precursor of the group $R^2$ to displace the group Y and produce a compound of formula III:

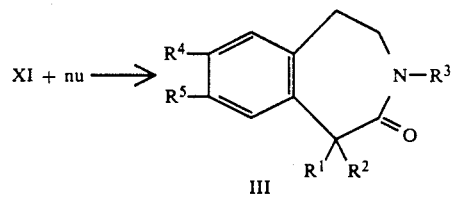

The reaction conditions for these two steps are as described above in the preceding paragraph. Also, the order of reactions of the nucleophiles may be reversed so that the $R^2$ group is added first and the $R^1$ group second.

As another alternative, the compound of formula VIII may be reacted in an electrophilic substitution reaction with a compound of the formula $R^1L^1$ wherein $L^1$ is a leaving group such as a halogen, e.g., Cl, Br or I, or a sulfononyloxy group, e.g., tosyloxy, methanesulfonyloxy, etc., to produce a compound of the formula X:

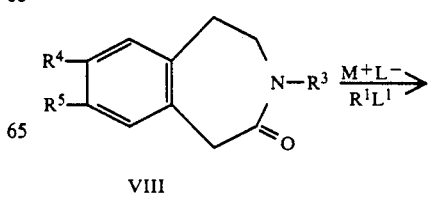

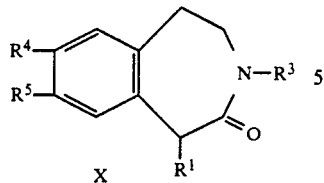

This reaction is run in the presence of a strong base M+L− such as NaH, KH, potassium tertiary butoxide, etc. The reaction may be performed at temperatures of from about 0° C. to about 100° C, may and may be run neat or in an inert solvent such as THF, DMF, etc.

If it is desired that $R^2$ be other hydrogen, a compound of formula X may be reacted in another electrophilic substitution reaction with a compound $R^2L^1$ wherein $L^1$ is as described above to produce a compound of formula III:

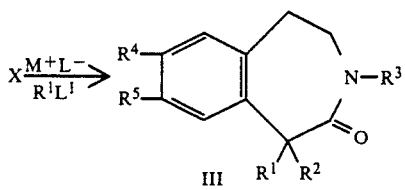

This second electrophilic substitution is performed under basically the same conditions as described in the previous paragraph. Again, the order of reaction of the $R^1L^1$ and $R^2L^1$ reactants may be reversed so that the $R^2$ group is added first and the $R^1$ group second.

The compounds of formula VII above may also be converted directly to a compound of formula I by employing a stronger reducing agent which will reduce both the olefinic bond and the carbonyl group of the compound of formula VII:

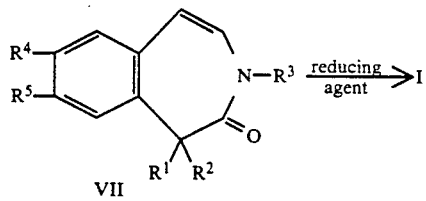

Suitable stronger reducing conditions include, for example, catalytic hydrogenation under elevated temperature and pressure, e.g., with Raney nickel at about 25° to about 100° C. and about 20-100 atmospheres. These reductions may be performed in inert solvent such as ethanol.

B. To produce a compound of formula I wherein $R^3$ is $CH_3$, a compound of formula XII may be reduced to give a compound of formula XIII:

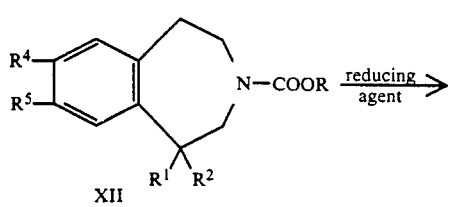

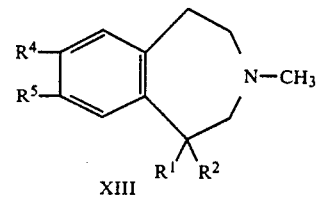

wherein R is an alkyl or aryl group such as methyl, ethyl, phenyl, etc. Any suitable reducing agent may be employed, e.g., $LiAlH_4$, etc., in a suitable solvent such as ether, THF, etc. and at a temperature of from 0° C. up to reflux temperature of the reaction mixture.

The compound of formula XII may be prepared by a number of different techniques. For example, a compound of XIV may be reacted with a compound of XV to produce a compound of XVI:

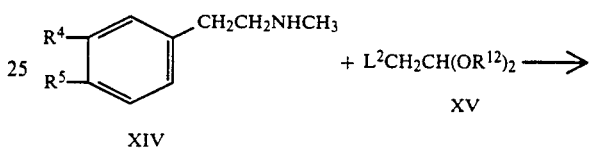

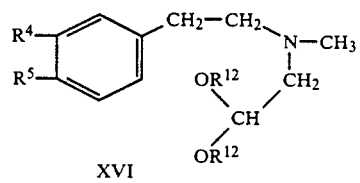

In formula XV $L^2$ represents a suitable leaving group such as Cl, Br, I, tosyloxy, methanesulfonyloxy, etc. and $R^{12}$ represents alkyl. Any inert solvent such as ether, $CH_2Cl_2$, $CHCl_3$, etc. may be employed.

The compound of formula XVI may be cyclized with a strong acid such as HCl, $CF_3SO_3H$, etc. to produce compounds of formulas XVII and XVIII (the compounds XVII also being final compounds of the formula I prepared in accordance with Process D of the invention hereinafter described in greater detail):

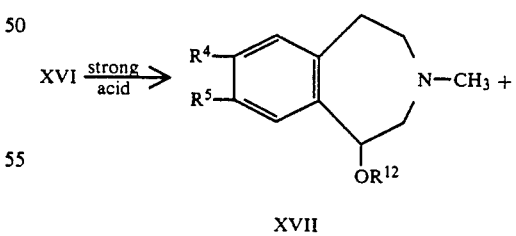

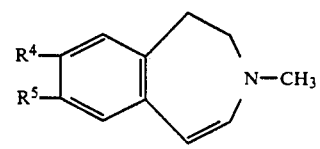

The compound of formula XVII is separated and reacted with a compound of formula

and then with an oxidizing agent as ceric ammonium nitrate and sodium bromate to produce a compound of formula XIX:

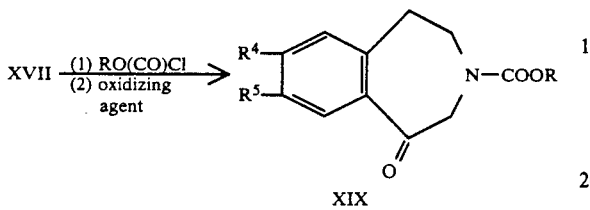

The carbonyl group on the compound of formula XIX may be reduced to a hydroxyl group with a suitable reducing agent, for example, NaBH₄, to produce a compound of formula XX:

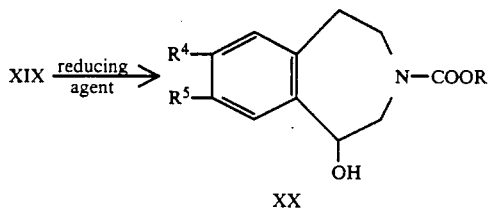

To convert a compound of formula XX to a compound of formula XIIa wherein $R^1$ is $OR^{6a}$, $R^{6a}$ is phenyl, substituted phenyl or naphthyl, and $R^2$ is H, the compound of formula XX is reacted with a compound of formula $R^{6a}OH$ is the presence of diethylazodicarboxylate (DEAD):

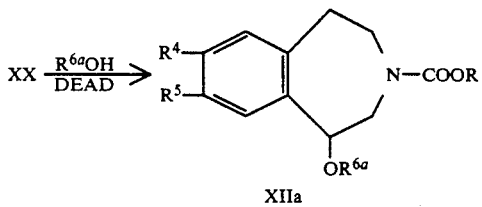

To convert a compound of formula XX to a compound of formula XIIb wherein $R^2$ is H, $R^1$ is $R^{1a}$ and $R^{1a}$ is $R^1$ other than $OR^{6a}$, a compound of formula XX is reacted with a sulfonyl halide such as tosyl chloride (TsCl) to form a compound of formula XXI. The compound of formula XXI is then reacted with a suitable nucleophile (nu) which is the precursor of the $R^{1a}$ group, e.g., $HNR^6R^{10}$ such as methyl amine, an alkanol such as methanol, ethanol or benzyl alcohol, a thiol such as methanethiol, a cyanide such as NaCN, etc, to provide a compound of formula XIIb:

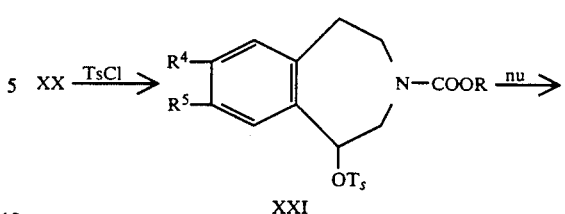

To convert the compounds of formulas XIIa and XIIb to a compound of formula XII wherein $R^2$ is other than H, the reactions described in the preceding two paragraphs are repeated with a nucleophile suitable to provide the desired $R^2$ group. Again, the additions of the $R^1$ and $R^2$ group may be reversed.

C. A compound of formula XXIIa or XXIIb may be reacted with a compound $R^2L^3$ or $R^1L^3$, respectively, and then with a suitable hydrogenating agent such as NaBH₄, in an agent medium such as a lower alcohol and at a temperature of from 0° C. up to the reflux temperature of the reaction mixture, to provide a compound of formula I:

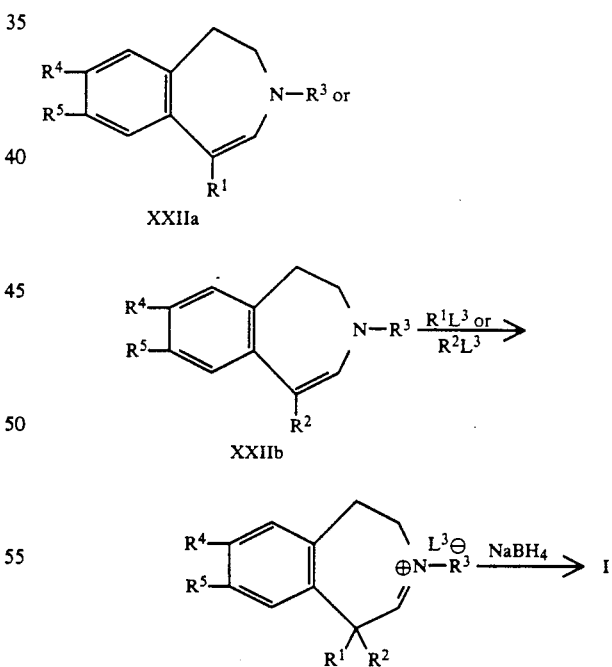

wherein $L^3$ represents a suitable leaving group such as an anion derived from a halo acid or sulfonic acid, e.g Br, tosyloxy, Cl, etc.

The compounds of formula XXIIa or XXIIb may be prepared by reacting a compound of formula XVIII with a suitable electrophilic agent $R^1L^3$ or $R^2L^3$, respectively, wherein $L^3$ is as defined above. Suitable electrophilic agents include, for example, benzyl bromide. This reaction may be run in the presence of a base such as potassium carbonate and in the presence in an inert solvent such acetonitrile.

By another process, Process E, where it is desired to produce a compound of formula XXIIIa or XXIIIb

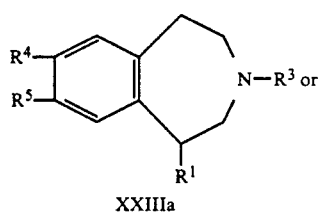
XXIIIa

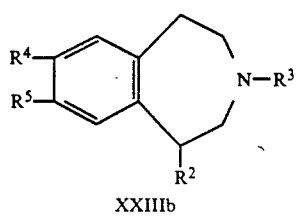
XXIIIb the olefinic double-bonds of the compounds of formula XXIIa and XXIIb may be saturated by techniques conventional in the art, for example, by treatment with sodium borohydride in the presence of a carboxylic acid, e.g., acetic acid in an inert medium at a temperature of from 0° C. up to the reflux temperature of the reaction mixture.

D. The compounds of the general formula I may also be prepared by intramolecular condensation of a compound of the general formula

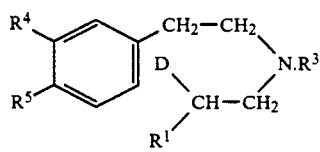
XVI' where D is a reactive group capable of being eliminated as DH with formation of the azepine ring. Typically D may be hydroxy, a substituted hydroxy group, in particular alkoxy, a halogen such as chlorine or bromine or a sulfonic acid ester such as —O—tosyl or an —O—mesyl group. Condensation may suitably be effected by treating the compound of the general formula XVI' with a strong acid such as HCl, $CF_3SO_3H$ in an inert medium at a temperature of from 0° C. up to the reflux temperature of the reaction mixture and then isolating the desired compound of the formula I.

As a finishing step, a compound of formula XXIV may be reacted with a compound of formula XXV to produce a compound of formula I:

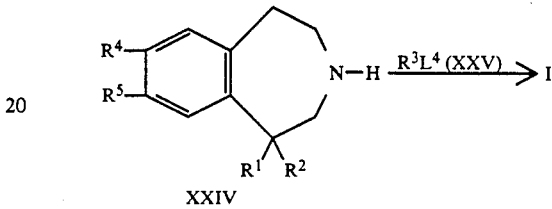
XXIV wherein $L^4$ is a leaving group such as Br, tosyloxy, Cl, etc. The compounds of formula XXIV above may be prepared, for example, by treating a compound of formula XII with hydrolyzing agent such as a base, e.g., aqueous or alcoholic KOH or NaOH.

In the above processes A-E, it is sometimes desirable and/or necessary to protect certain $R^1$, $R^2$, $R^3$, $R^4$ and $R^5$ groups during the reactions. Conventional protecting groups are operable. For example, the groups listed in column 1 of the following table may be protected as indicated in column 2 of the table:

| 1. Group to be Protected | 2. Protected Group |
|---|---|
| —COOH | —COOalkyl, —COObenzyl, —COOphenyl |
| \NH/ | \N—CO₂alkyl/, \N—CO₂benzyl/, \N—CO₂CH₂CCl₃/ |
| \CO/ | (cyclic acetal structures) |
| —OH | —O-(tetrahydropyranyl), —OCH₃ |
| —NH₂ | (phthalimide structure) |

Of course, other protecting groups well known in the art may be used. After the reaction or reactions, the protecting groups may be removed by standard procedures.

Also, $R^1$, $R^2$, $R^3$, $R^4$ and $R^5$ groups in formula I may be varied by appropriate selection of starting materials from which the compounds are synthesized or by reacting a compound of formula I with a suitable reagent to effect the desired conversion of the substituent to another $R^1$, $R^2$, $R^3$, $R^4$ or $R^5$ group.

The utility of the compounds of formula I may be demonstrated by test procedures designed to indicate their anti-psychotic and anti-depressive activity.

CONDITIONED AVOIDANCE SUPPRESSION IN RATS

Clinically active antipsychotic drugs are known to depress discrete trial avoidance behavior at doses that do not retard escape response {Ann. N. Y. Acad. Sci. 66, 740 (1957)}. A series of experiments was carried out to assess the ability of the compounds of this invention to suppress the conditioned avoidance response (CAR) in rats.

Materials and Methods

Rats were required to jump onto a platform located 6.75 inches (17.15 cm) above the grid floor of an experimental chamber in response to a 5-second tone to avoid a 10-second foot shock (0.6 ma). Each experimental session consisted of 20 such trials presented at 30-second intervals. A correct CAR is scored whenever the rat jumps onto the platform during the tone (prior to foot shock). An escape response is scored when the rat jumps onto the platform during a shock. A response failure is defined as the lack of an escape response during the 10-second shock period.

Groups of 6-8 rats were trained in two consecutive days (total of 40 trials). Rats that reached criterion on day 2 (correct CARs on 16 or more of the 20 trials) were treated with either a test drug or vehicle on day 3. Suppression of CAR was analyzed statistically using Student's t-test comparing the performances of drug-treated to vehicle-treated rats. The minimal effective dose (MED) for each drug is defined as the lowest dose tested that significantly ($P<0.05$) reduced avoidance responding.

Results

Representative compounds of the invention when tested by the above procedure manifested a dose-related specific blockade of conditioned avoidance response as set forth in Table 1 below:

TABLE 1

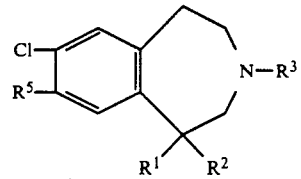

| Compound No. | $R^5$ | $R^1$ | $R^2$ | $R^3$ | Rat CAR (mg/kg) sc | Rat CAR (mg/kg) po |
|---|---|---|---|---|---|---|
| 1 | HO— | —OCH$_3$ | —H | —CH$_3$ | 1 | >30 |
| 2 | HO— | —OC$_2$H$_5$ | —H | —CH$_3$ | 1 | >30 |
| 3 | HO— | —SC$_2$H$_5$ | —H | —H | <10 | — |
| 4 | HO— | —OPh* | —H | —CH$_3$ | — | 10 |
| 5 | HO— | —SPh* | —H | —CH$_3$ | >30 | >30 |
| 6 | HO | 1-piperidinyl | —H | —CH$_3$ | 3 | 30 |
| 7 | HO | 1-imidazolyl | —H | —CH$_3$ | >10 | >30 |
| 8 | HO | cyclohexyl | —H | —CH$_3$ | ≦1 | 30 |
| 9 | HO | OCH$_2$CF$_3$ | —H | —CH$_3$ | 1 | >30 |
| 10 | HO | OCH$_2$C$_6$H$_5$ | —H | —CH$_3$ | 3 | >30 |
| 11 | HO | O(CH$_2$)$_2$Ph | —H | —CH$_3$ | 1 | >30 |
| 12 | HO | cyclopentyl | —H | —CH$_3$ | 1 | >30 |
| 13 | HO | 1-pyrrolyl | —H | —CH$_3$ | 0.3 | >30 |
| 14 | HO | allyl | —H | —CH$_3$ | 0.1 | >30 |
| 15 | HO | —(CH$_2$)$_4$— | | —CH$_3$ | 1 | >30 |
| 16 | EtOCO$_2$ | cyclohexyl | —H | —CH$_3$ | <3 | >30 |
| 17 | i-PrCO$_2$ | allyl | —H | —CH$_3$ | 0.3 | >30 |
| 18 | MeOCH$_2$CO$_2$ | allyl | —H | —CH$_3$ | <0.3 | 100 |
| 19 | CH$_3$CO$_2$ | 3,3-diMe-2-allyl | —H | —CH$_3$ | <1 | >30 |
| 20 | POM** | allyl | —H | —CH$_3$ | 0.1 | >30 |

*Ph = phenyl
**POM = t-Bu.COO.CH$_2$O—

COMPETITIVE INHIBITION ASSAY

Many compounds capable of effecting reproducible physiological changes in neural tissues are believed to operate by binding at one or more receptor sites. Compounds which interact strongly with these receptor sites in in vitro tests, using homogenates of the target organ or structure, are expected to exhibit similar properties when administered in vivo and are, therefore, candidates for continued study as potential therapeutic and/or diagnostic agents.

Binding of a compound to a receptor site, in vitro, is demonstrated by the specificity of binding and for characterization of binding and an interpretation of the data are described by Billard et al., *Life Sciences* 35, 1885 (1984) in which the binding of the benzazepine (R)-(+)-8-chloro-2,3,4,5-tetrahydro-3-methyl-5-phenyl-1H3-benzazepin-7-ol hemimaleate (SCH 23390) to the dopamine D-1 receptor is characterized.

Materials and Methods

Tritiated SCH 23390 and tritiated spiperone (a potent D-2 ligand) were obtained as described in the Billard et al. reference supra and serially diluted in 0.05 M Tris buffer, pH 7.4, as required. A compound of the invention is diluted in 0.05 M Tris buffer, pH 7.4, as required.

Tissue Preparation

Male Sprague-Dawley rats (200 to 250 g) from Charles River Breeding Laboratories, Mass. were used to obtain brain tissue. The rats were humanely sacrificed and their brains removed and placed on ice. Striatal tissue was excised, pooled, and homogenized (Brinkman Polytron, 10 sec) in 100 volumes (w/v) of ice cold 50 mM Tris buffer, pH 7.4 (at 25° C.). The homogenate was centrifuged at 20,000 xg for 10 min. The resultant pellet was rehomogenized in Tris buffer and centrifuged again. The final pellet was resuspended in 50 mM Tris buffer pH 7.4 containing 120 mM NaCl, 5 mM KCl, 2 mM CaCl$_2$, and 1 mM MgCl$_2$.

Assay

Polypropylene incubation tubes received 100 μl of the individual test compounds at various concentrations dissolved or suspended in 0.05 M Tris, pH 7.4 containing 4 mg/ml methylcellulose, 100 μl of a solution of $^3$H-SCH 23390 in Tris buffer (final reaction mixture concentration =0.3 nM) or 100 μl of a solution of 3H-spiperone in Tris buffer (final concentration =0.2 nM) and 800 μl of tissue suspension (ca. 3 mg/assay). Tubes were incubated at 37° C. for 15 minutes and rapidly vacuum filtered through Whatman GF/B filters and rinsed 4 times with 4 ml of ice cold 50 mM Tris buffer, pH 7.4. The filters were transferred to scintillation vials, equilibated with 10 ml of scintillant (Scintosol, Isolab, Inc.) for 16 hours at 25° C. and the radioactivity determined in a liquid scintillation counter. K$_i$ values were determined as described by Billard et al. using the relationship K$_i$=IC$_{50}$/(1+([L]/K$_D$)) wherein IC$_{50}$=concentration of test drug necessary to displace 50% of specifically bound $^3$H-Sch 23390, [L]=concentration of radioligand used in the assay, and K$_D$=dissociation constant.

Results

The inhibition constants (K$_i$) determined from the assays for compounds of the invention are as shown in Table 2 below.

TABLE 2

| | | | | K$_i$ (nM) vs. | |
|---|---|---|---|---|---|
| R$^5$ | R$^3$ | R$^1$ | R$^2$ | $^3$H-SCH 23390 | $^3$H-spiperone |
| HO— | —CH$_3$ | —OCH$_3$ | —H | 54 | 5600 |
| HO— | —CH$_3$ | —OC$_2$H$_5$ | —H | 34 | 7720 |
| HO— | —CH$_3$ | —SC$_2$H$_5$ | —H | 33 | 2612 |
| HO— | —H | —SC$_2$H$_5$ | —H | 380 | 6500 |
| HO— | —CH$_3$ | =CHPh* | — | 73 | 705 |
| HO— | —CH$_3$ | —OPh* | —H | 83 | 610 |
| HO— | —CH$_3$ | —SPh* | —H | 33 | 402 |
| HO— | —CH$_3$ | 1-piperidinyl | —H | 64 | 7500 |
| HO— | —CH$_3$ | cyclohexyl | —H | 10 | 570 |
| HO— | —CH$_3$ | —(CH$_2$)$_3$N(CH$_3$)$_2$ | —H | 1100 | >100,000 |
| HO— | —CH$_3$ | cyclohexyloxy | —H | 38 | 10,100 |
| HO— | —CH$_3$ | 2-cyclohexenyl | —H | 1.1 | 135 |
| HO— | —CH$_3$ | OCH$_2$CF$_3$ | —H | 59 | 14,900 |
| HO— | —CH$_3$ | OCH$_2$C$_6$H$_5$ | —H | 30 | 2300 |
| HO— | —CH$_3$ | O(CH$_2$)$_2$Ph | —H | 8 | 1020 |
| HO— | —CH$_3$ | cyclopentyl | —H | 21 | 1538 |
| HO— | —CH$_3$ | 1-pyrrolyl | —H | 11 | 16,100 |
| HO— | —CH$_3$ | allyl | —H | 6 | 170 |
| HO— | —CH$_3$ | —(CH$_2$)$_4$— | | 19 | 860 |
| EtOCO$_2$ | —CH$_3$ | cyclohexyl | —H | 133 | 3334 |
| i-PrCO$_2$ | —CH$_3$ | allyl | —H | 84 | 3447 |
| MeOCH$_2$CO$_2$ | —CH$_3$ | allyl | —H | 10.3 | 566 |
| CH$_3$CO$_2$ | —CH$_3$ | 3,3-diMe-2-allyl | —H | 17 | 955 |
| POM** | —CH$_3$ | allyl | —H | 240 | 2620 |

*Ph = phenyl
**POM = t-Bu.COO.CH$_2$O—

The comparatively small K$_i$ values of these compounds in the competitive binding assay with SCH 23390 indicate that the compounds of formula I bind strongly to the D-1 receptor site. The relatively high K$_i$ values for the D-2 site, for which spiperone is highly selective, indicates that the compounds are not specifically bound to that receptor site.

The antidepressive method of the invention is identified, for example, by test procedures which measure a compound's effect on tetrabenazine (TBZ)-induced ptosis in mice or which measure a compound's effect on muricide activity in rats as discussed below.

ANTIDEPRESSANT POTENTIAL

EFFECTS ON TETRABENAZINE (TBZ)—INDUCED PTOSIS IN MICE

Clinically active antidepressant drugs are known to block TBZ-induced ptosis in mice (Psychosomatic Medicine, Nodine and Moyer, Eds., Lea and Febiger, Philadelphia, 1962, pp 683–90). Activity in this test is used to predict anti-depressant activity in man.

Methods and Materials

Groups of 5 mice are administered test drugs followed 30 minutes later by ip injection of tetrabenazine, 30 mg/kg. Thirty minutes later, the degree of ptosis is evaluated. Percent blockade of each treated group is used to determine $ED_{50}$'s, defined as that dose which prevents ptosis in 50% of mice. $ED_{50}$'s and 95% confidence limits are calculated by probit analysis.

EFFECTS ON MURICIDAL BEHAVIOR IN RATS

Blockade of muricidal (mouse-killing) behavior in rats is used as a measure of evaluating the antidepressant activity of drugs (Int. J. Neuro-pharmacol., 5, 405-11 (1966)).

Methods and Materials

Groups of 5 rats are administered test drug intraperitonially and are tested 30 and 60 minutes later for presence of muricidal behavior. Percent blockade of each treated group using data obtained at both these time points is calculated and dose-response data are used to determine each $ED_{50}$. $ED_{50}$ is defined as that dose which blocks muricide behavior in 50% of treated rats and is calculated using probit analysis.

The analgesic effect of the compounds of formula I and the method for providing analgesia may be exemplified by the Acetic Acid Writing Test in Mice described below.

ACETIC ACID WRITHING TEST IN MICE

The blockade of writhing induced by the intraperitoneal injection of acetic acid is an established experimental animal model for the screening of antinociceptive drugs (drugs which prevent the appreciation or transmission of pain sensations). See Hendershot et al., *J. Pharmacol. Exp. Therap.* 125:237, (1959) and Koster et al., *Fed. Proc.* 18:412, (1959).

METHODS AND MATERIALS

Compounds to be tested are dissolved or suspended in aqueous 0.4% methylcellulose vehicle. For oral administration, dosages are prepared for delivery of the selected weight of compound in a total volume of 20 mg/kg of body weight. For subcutaneous or intraperitoneal administration, dosages are prepared for delivery of the selected weight of compound in a volume of 10 ml/kg of body weight.

The test procedure is that described by Hendershot et al., supra, except that acetic acid is substituted for phenylquinone. Groups of five male CF1 mice (20-26 g.) are dosed orally with test drug and injected 15 minutes later with 0.6% aqueous acetic acid (10 mg/kg). The mice are placed in a large observation beaker and the number of writhes for each animal is counted during a 10 minute interval starting 3 minutes after injection of acetic acid. A writhe is defined as a sequence of arching of the back, pelvic rotation and hindlimb extension. Initial screening is performed using a dosage of 30 mg/kg. If this dose affords 50% or greater reduction in the number of writhes compared to the control, the animal is considered to be protected, a dose response curve is developed using a logarithmic sequence of lower doses and an ED50 is determined by interpolation.

Regarding toxicity, the compounds of this invention are non-toxic at the therapeutic dose.

For preparing pharmaceutical compositions from the compounds of formula I, inert, pharmaceutically acceptable carriers are admixed with the active compounds. The pharmaceutically acceptable carriers may be either solid or liquid. Solid form preparations include powders, tablets, dispersible granules, capsules, cachets and suppositories. A solid carrier can be one or more substances which may also act as diluents, flavoring agents, solubilizers, lubricants, suspending agents, binders or tablet disintegrating agents; it may also be an encapsulating material. In powders, the carrier is a finely divided solid which is in admixture with the finely divided active compound. In the tablet, the active compound is mixed with a carrier having the necessary binding properties in suitable proportions and compacted in the shape and size desired. The powders and tablets typically contain from 5 to about 70% of the active ingredient dependent upon the potency of the active compound, the size and age of the intended user, and the range of dosage required for the specific therapy. Suitable solid carriers are magnesium carbonate, magnesium stearate, talc, sugar, lactose, pectin, dextrin, starch, gelatin, tragacanth, methylcellulose, sodium carboxymethylcellulose, a low melting wax, cocoa butter and other materials typically used in the pharmaceutical industries. The term "preparation" is intended to include the formulation of the active compound with encapsulating material as carrier, providing a capsule in which the active component (with or without other carriers) is surrounded by a carrier, which is thus in association with it. Similarly, cachets are included. Tablets, powders, cachets and capsules can be used as solid dosage forms suitable for oral administration.

For preparing suppositories, a low melting wax such as a mixture of fatty acid glycerides or cocoa butter is first melted and the active ingredient is dispersed homogeneously therein as by stirring. The molten homogeneous mixture is then poured into convenient sized molds, allowed to cool and thereby solidify.

Liquid form preparations include solutions, suspensions and emulsions. As an example may be mentioned water or water-propylene glycol solutions for parenteral injection. Liquid preparations can also be formulated in solution in aqueous polyethylene glycol solution. Aqueous solutions suitable for oral use can be prepared by adding the active component in water and adding suitable colorants, flavors, stabilizing, sweetening, solubilizing and thickening agents as desired. Aqueous suspensions suitable for oral use can be made by dispersing the finely divided active component in water with viscous material, i.e., natural or synthetic gums, resins, methylcellulose, sodium carboxymethylcellulose and other well-known suspending agents.

Also included are solid form preparations which are intended to be converted, shortly before use, to liquid form preparations for either oral or parenteral administration. Such liquid forms include solutions, suspensions and emulsions. These particular solid form preparations are most conveniently provided in unit dose form and as such are used to provide a single liquid dosage unit. Alternatively, sufficient solid may be provided so that after conversion to liquid form, multiple individual liquid doses may be obtained by measuring predetermined volumes of the liquid form preparation as with a syringe, teaspoon or other volumetric container. The solid form preparations intended to be converted to liquid form may contain, in addition to the active material, flavorants, colorants, stabilizers, buffers, artificial and natural sweetners, dispersants, thickeners, solubilizing agents and the like. The solvent utilized for preparing the liquid form preparation may be water, isotonic aqueous salt solutions, ethanol, glycerine, propylene glycol and the like, as well as mixtures thereof. The solvent utilized will be chosen with regard to the route of administration. For example, liquid preparations containing large amounts of ethanol are not generally suitable for parenteral use.

The invention also contemplates alternative delivery systems including, but not necessarily limited to, transdermal delivery. The transdermal compositions can take the form of creams, lotions and/or emulsions and can be included in a transdermal patch of the matrix or reservoir type as are conventional in the art for this purpose.

Preferably, the pharmaceutical preparation is in unit dosage form. In such form, the preparation is subdivided into unit doses containing appropriate quantities of the active components. The unit dosage form can be a packaged preparation, the package containing discrete quantities of preparation such as packeted tablets, capsules and powders in vials or ampules. The unit dosage form can also be a capsule, cachet or tablet itself, or it may be the appropriate number of any of these in a packaged form.

The quantity of active compound in a unit dose preparation may be varied or adjusted from 1 mg to 100 mg according to the particular application and the potency of the active ingredient and the intended treatment. A dose of about 0.02 to about 2.0 mg/kg, preferably about 0.02 to about 0.2 mg/kg, may be employed and may be divided over 1 to 3 administrations per day. The composition may, if desired, also contain other therapeutic agents.

The dosages may be varied depending on the requirement of the patient, the severity of the condition being treating and the particular compound being employed. Determination of the proper dosage for a particular situation is within the skill of those in the medical art. For convenience, the total daily dosage may be divided and administered in portions throughout the day or by means providing continuous delivery.

The invention disclosed herein is exemplified by the following examples which should not be construed to limit the scope of the disclosure. Alternative mechanistic pathways and analogous structures within the scope of applicants' invention may be apparent to those skilled in the art.

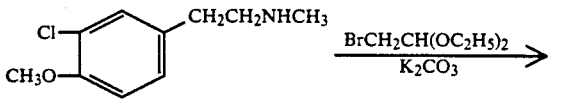

A

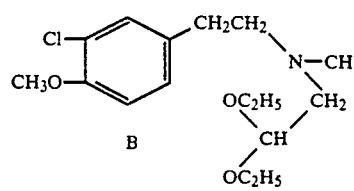

B

A mixture of 30.0 g of the compound of formula A above, 32.8 g of bromoacetaldehyde diethylacetal, 50 g of anhydrous K$_2$CO$_3$ and 150 ml dry dimethylformamide (DMF) were stirred and heated under nitrogen to 120° C. After two hours, the solution was filtered, and the filtrate poured into water. The mixture was extracted twice with 200 ml of ether, the combined ether layers washed with brine, dried and concentrated to a oil (38.4). Thin layer chromotography showed the compound of formula B above as the only major product, R$_f$=0.73 developed with CHCl$_3$/CH$_3$OH/NH$_4$OH—1000:40:3.

EXAMPLE 1

Step A

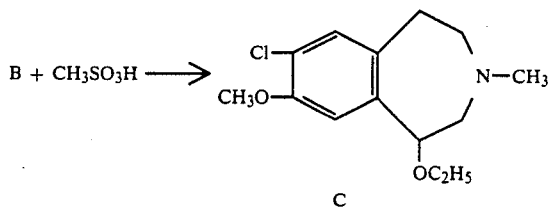

C

The compound of formula B (3.4 g) prepared as described in Preparative Example 1 was mixed at ice-bath temperature with 10 ml of methanesulfonic acid, and the resulting solution then heated to 70° C. After two hours, the resulting mixture was poured into cold excess saturated NaHCO$_3$ solution. The mixture was extracted with ether. The extracts were washed with brine, dried and concentrated to an oil (2.7 g). The product was dissolved in ether and treated with a slight excess of ethereal HCl. A yellow gum separated and crystallized. Filtration of the solid and recrystallization from 2-butanone gave the compound of formula C above as a hydrochloride salt, m.p. 195°–197° C.

Step B

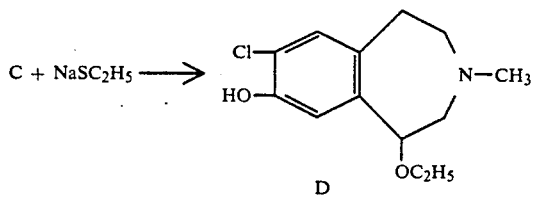

D

The compound of formula C (750 mg) prepared in Example 1A in 20 ml of dimethylformamide was added dropwise to a solution prepared from 60% sodium hydride in mineral oil (490 mg) and ethanethiol (0.9 ml) in 20 ml of dimethylformamide. The resulting mixture was heated at 130° C. for ten hours, poured into water, and extracted with ether. The aqueous layer was then acidified to pH 1 with HCl and extracted again with ether. The aqueous layer was rebasified with solid NaHCO$_3$ and the precipitated oil extracted with ethyl acetate. The extract was washed with brine, dried over anhydrous MgSO$_4$, and concentrated to an oil, which was dissolved in ether and treated with ethereal HCl. The precipitated salt was separated by decantation, and recrystallized from acetone to give the compound of formula D above as a hydrochloride salt, m.p. 235°–236° C.

By employing basically the same process as described in Example 1, using an appropriate dimethylacetal of bromoacetaldehyde, the following 5-alkoxy-benzazepine-7-ol was prepared:

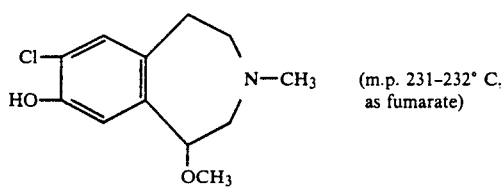

(m.p. 231-232° C. as fumarate)

PREPARATIVE EXAMPLE 2

Step A

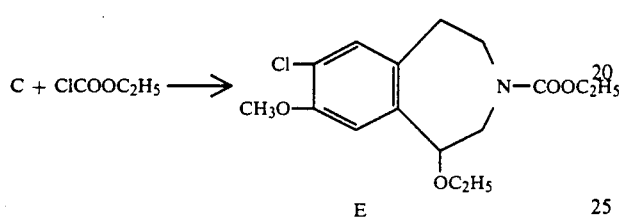

A solution of the compound of formula C above (19.5 g) in 250 ml of benzene was treated at reflux with 20.7 ml of ethyl chloroformate. The resulting solution was heated for three hours at reflux, the solvent then removed in vacuo, and the residue partitioned between ether and 5% HCl. The ether layer was separated, washed with brine, dried and concentrated to a dark gum, which was dissolved in petroleum ether, treated with Darco and Florisil and filtered. The filtrate was concentrated to a yellow oil (16.9 g). Thin layer chromotography showed the compound of formula E above as a single spot, $R_f=0.46$ (hexane/ethylacetate—2:1).

Step B

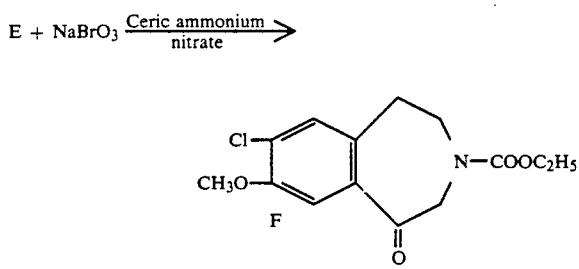

The compound of formula E above (16.9 g) was dissolved in 175 ml of acetonitrile and treated with a solution of 8.45 g of sodium bromate and 548 mg of ceric ammonium nitrate in 75 ml of water. The two-phase mixture was stirred at reflux for 24 hours.

The cooled mixture was diluted with 250 ml of water and extracted twice with 250 ml of ether. The ether phase was washed with brine, dried and concentrated to a gum. Trituration with ether/petroleum ether afforded the compound of formula F as prisms (6.0 g), m.p. 134°-135° C.

EXAMPLE 2

Step A

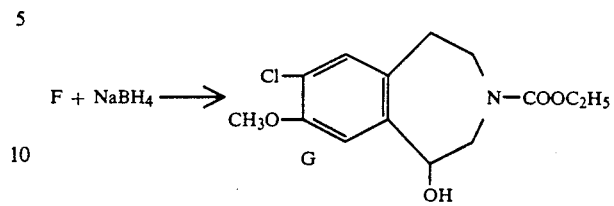

The compound of formula F above (1.0 g) (prepared as described in Preparative Example 2B and wherein $R^1$ together with $R^2$ represent carbonyl) was suspended in 20 ml of absolute ethanol and treated with 140 mg of sodium borohydride, portionwise, with stirring. The mixture was warmed to 40° C. and stirred for 20 minutes, after which 10 ml of 5% HCl and about 10 g of ice were added. After stirring another 30 minutes, the solid product was filtered, and dried to give 930 mg of the compound of formula G above, m.p. 143°-144° C.

Step B

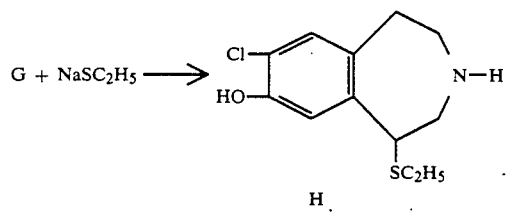

A solution of 0.45 g of the compound of formula G above in 10 ml of dry dimethylformamide was added to a solution of sodium thioethoxide prepared from 287 mg 60% NaH/mineral oil and 0.56 ml of ethanethiol in 10 ml of dimethylformamide. The resulting solution was heated at 125° C. overnight. It was then poured into water, and extracted with ether. The aqueous phase was acidified to pH 1 and rebasified with solid NaHCO3. The oily product was extracted with ethyl acetate and the solution evaporated to give the compound of formula H above as a crude product (0.4 g). This compound was converted to its hydrochloride by treatment of an ethereal solution with a slight excess of ethereal HCl. The resulting salt was filtered and dried in vacuo to produce a white amorphous solid.

EXAMPLE 3

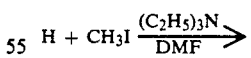

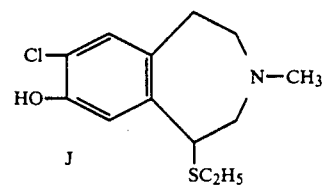

The compound of formula H (0.4 g), prepared as described in Example 2, was dissolved in 5 ml of dimethylformamide, 0.2 ml of triethylamine added, followed by 0.093 ml of methyliodide. The resulting mixture was allowed to stand at room temperature overnight, after which it was poured into water. The mixture was extracted with ethyl acetate, dried and concentrated to an oil. This material (250 mg) was chromotographed on 25 g Merck silica gel 60-G, eluting with CHCl₃/CH₃OH/ NH₄OH-1000:50:3. A component, TLC homogeneous ($R_f$=0.69, same solvent system), was obtained (105 mg) which was dissolved in ether and treated with an ethereal solution of 45 mg maleic acid. The precipitated solid was filtered and dried in vacuo to give 88 mg of the compound of formula J above as the maleate salt.

Analytically calculated for $C_{13}H_{18}NOSCl.C_4H_4O_4$: C 52.64; H 5.72; N 3.61. Found: C, 52.14; H, 5.60; N, 3.46. FAB mass spectrum m/e+1=272.

PREPARATIVE EXAMPLE 4

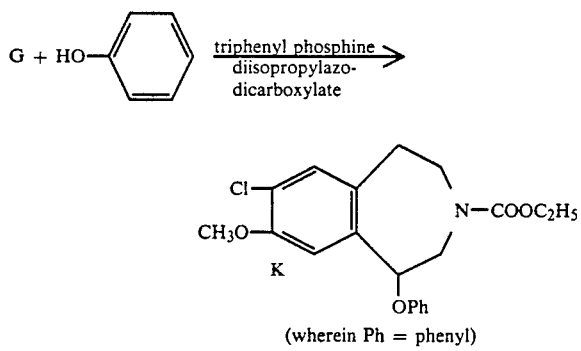

(wherein Ph = phenyl)

Triphenylphosphine (0.57 g) and phenol (0.21 g) were added to a solution of the compound of formula G (0.6 g), prepared as described in Example 2A, in 30 ml of benzene. To this solution was then added another solution of diisopropylazodicarboxylate (0.433 ml) in 10 ml benzene over five minutes. The resulting mixture was allowed to stand at room temperature overnight, after which it was concentrated to a gum. This product was chromotographed on 100 g Merck silica gel 60 G, eluting with ethylacetate/hexane-1:4, to give 0.5 g of the compound of formula K above as a yellow oil.

EXAMPLE 4

Step A

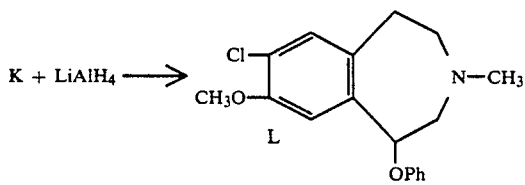

The compound of formula K above (430 mg) in 20 ml of ether was added to a suspension of lithium aluminum hydride (53 mg) in 20 ml of ether. The mixture was allowed to stir at room temperature for three hours, and was then decomposed by treatment with cold 10% NaOH solution until all solids dissolved and the phases separated. The aqueous phase was extracted with ethyl acetate and the combined organic layers washed with brine, dried and concentrated to an oil (350 mg) which solidified on drying overnight in vacuo to provide the compound of formula L above.

Step B

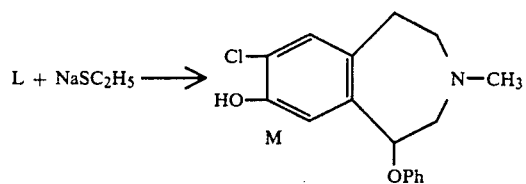

A solution of the compound of formula L above (350 mg) in 10 ml of dimethylformamide was added dropwise to a solution of sodium thioethoxide prepared from 132 mg 50% NaH/mineral oil dispersion and 0.408 ml of ethanethiol in 5 ml of dimethylformamide. The resulting mixture was stirred for three hours at 100° C. under a nitrogen atmosphere. Solvent was removed in vacuo, and the residue partitioned between water and ether to provide the compound of formula M above, m.p. 166°–168° C.

By employing in Preparative Example 4 the substituted phenol listed in the first column of Table 3 below in place of phenol and basically the same processes as described in Preparative Example 4 and Example 4 above, the products listed in the second column of Table 3 may also be prepared:

TABLE 3

| Phenol | Product $R^1$ = |
|---|---|
| HO—⟨⟩—Cl | —O—⟨⟩—Cl |
| HO—⟨⟩(Br) | —O—⟨⟩(Br) |
| HO—⟨⟩(NO₂) | —O—⟨⟩(NO₂) |
| HO—⟨⟩—CH₃ | —O—⟨⟩—CH₃ |

Product structure:

Cl—⟨⟩—N—CH₃ / HO—, R¹

PREPARATIVE EXAMPLE 5

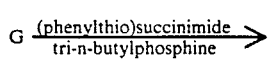

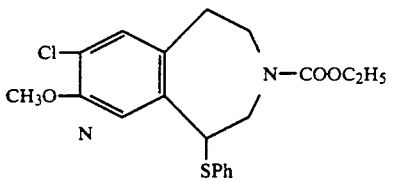

To a stirred solution of tri-n-butylphosphine (0.485 g, 2.4 mmole in benzene (10 ml) was added solid N-(phenylthio)succinimide (475 mg, 2.4 mmole) in one portion. The resulting solution was stirred at ambient temperature for five minutes, then the compound of formula G (554 mg, 1.8 mmole), prepared as described in Example 2A was added all at once. The mixture was stirred at ambient for about 12 hours. An additional 0.2 ml of tri-n-butylphosphine was added and stirred in an additional 2 hours.

The resulting mixture was concentrated to dryness and water and ether/hexane 1:1 were added. The organic phase was washed with brine, dried and concentrated to a gum, 0.8 g. The gum was chromotographed on about 8.0 g Merck silica gel G, eluting with hexane, then hexane/ethyl acetate 1:4 to yield 0.6 g of the compound of formula N above, which was characterized by NMR and TLC. ($R_f$=0.3 in ethyl acetate/hexane 1:3.)

EXAMPLE 5

Step A

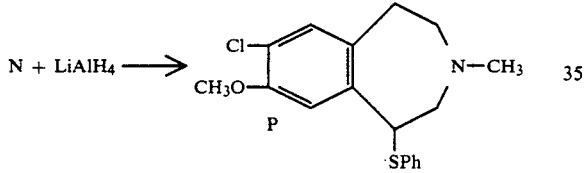

The chromatographed compound of formula N above from Preparative Example 5 (0.55 g, 1.4 mmole) in 20 ml ether was added to an ice-cooled slurry of 70 mg (1.8 mmole) lithium aluminum hydride in 20 ml of ether. The cloudy solution was stirred at ambient temperature for about 50 hours. An additional 40 mg of LiAlH$_4$ in ether was added. After 30 minutes TLC showed complete reaction. Cold 10% NaOH was added until all solids dissolved. The aqueous layer was separated and extracted with ethyl acetate. The combined organic layers were washed with brine, dried and concentrated to provide the compound of formula P above as a gum, 0.427 g.

Step B

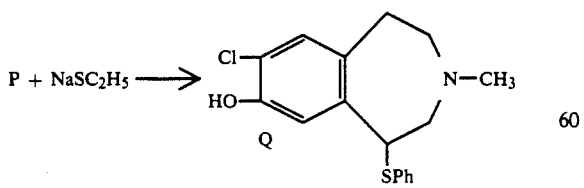

The compound of formula P above (0.42 g, 1.25 mmole) was added in 5 ml of DMF to a solution of sodium thioethoxide (prepared from 100 mg (2.5 mmole) NaH 60% in oil dispersion and 0.185 ml (2.5 mmole) ethanethiol in 10 ml DMF) and the clear solution stirred at 100°–110° C. for about 32 hours. An additional 2.5 mmole of sodium thioethoxide (prepared as above) was added and the reaction mixture heated an additional 3 hours at which time TLC showed virtually complete reaction.

The mixture was poured into water and extracted with hexane. The basic aqueous solution was acidified to pH 1 with 5% HCl and re-extracted with hexane. The acid phase was basified with solid NaHCO$_3$ and extracted with ethyl acetate to yield 400 mg of oily product. Upon standing, the material crystallized. The solid was recrystallized from ether/petroleum ether to yield 170 mg of the compound of formula Q above, m.p. 158°–60°.

PREPARATIVE EXAMPLE 6

Step A

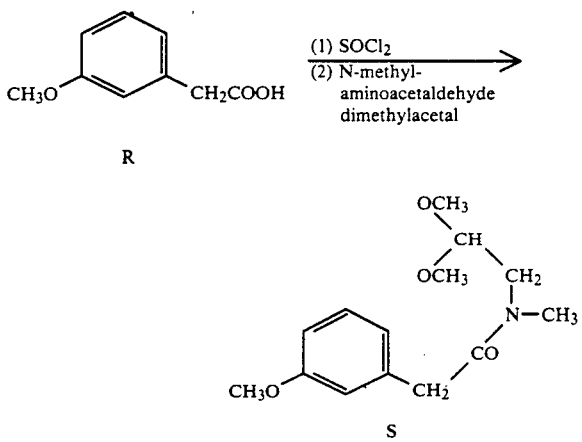

85 ml of thionyl chloride was added dropwise to a solution of 64.0 g of the acid of formula R above in 100 ml of dry dichloromethane with stirring. The mixture was stirred at room temperature for 3 hours longer and then heated on a steam bath under gentle refluxing for two hours. The low boiling material (solvent and excess SOCl$_2$) was distilled off at about 50° C. under vacuum. The residue was dried under vacuum at room temperature for 2 hours longer.

The concentrated acid chloride produced was dissolved in 120 ml of CH$_2$Cl$_2$ and then added dropwise to a stirring solution of 50 ml of N-methylaminoacetaldehyde dimethylacetal and 80 ml of triethylamine (50% excess) in 350 ml of methylene chloride for 1.5 hours at 20°–25° C. with occassional cooling. The mixture was stirred at room temperature for one hour longer. The reaction mixture was extracted twice with 500 ml of water, dried over MgSO$_4$, filtered and then rotoevaporated down to dryness to provide about 100 g of the compound of formula S above as a viscous syrup.

Step B

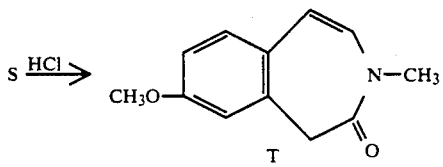

The viscous syrup was added in small portions to 500 ml of concentrated HCl (previously chilled in an ice bath) with cooling and stirring (ice bath) This was further diluted with 500 ml of acetic acid. The mixture was stirred at room temperature overnight. The reaction mixture was poured into 8 liters of ice and H₂O with stirring over 30 minutes. A gummy solid was filtered off and washed with water. The filtrate was extracted with one liter of CH$_2$Cl$_2$ and rotoevaporated down to dryness. The residue of the rotoevaporation and the wet gummy solid were combined and redissolved in 700 ml of ether. The ether was extracted twice with 300 ml of water, and the ether solution was dried over K$_2$CO$_3$, charcoaled, filtered and then rotoevaporated down to dryness to provide 68.0 g of a viscous syrup which crystallized out upon seeding to give the compound of formula T above.

Step C

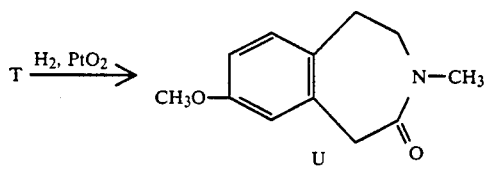

68.0 g of the material of formula T from Preparative Example 6B above were dissolved in 600 ml of ethanol which was then divided into two equal portions and each portion was reduced with H$_2$ over 2.5 g of PtO$_2$.

After removing the catalyst, the filtrates of both runs were combined, checked with TLC and rotoevaporated down to dryness. The residue was stirred with 150 ml of cold ethyl acetate with seeding. The solution was chilled in an ice bath, filtered and the solid was washed with cold ethyl acetate to provide about 28.0 g of the compound of formula U. 24.0 g of this material and 12.0 g from another batch were combined and dissolved in 100 ml of boiling ethyl acetate. The mixture was cooled in a freezer and filtered, and the solid was washed with cold ethyl acetate. The solid was dried at room temperature for one hour to provide 22.50 g of the compound of formula U, m.p. 104°–105° C.

Step D

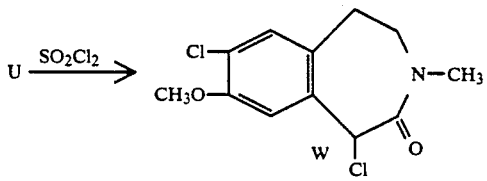

To a solution of the compound of formula U above in 300 ml of CH$_2$Cl$_2$ was added a solution of 15 ml of SO$_2$Cl$_2$ in 35 ml of CH$_2$Cl$_2$ in a period of about 25 minutes. The reaction mixture was stirred at room temperature for 2½ hours longer and poured into 500 ml of ice water with stirring. The organic layer was dried over MgSO$_4$, filtered and then rotoevaporated down to dryness. The residue crystallized out partially. The mixture was then triturated with 40 ml of cold ethyl acetate and filtered, and the solid which separated was washed with 10 ml of cold ethyl acetate to provide 13.90 g of the compound of formula W, m.p. 162°–164° C.

The filtrate was kept in a freezer overnight and then filtered to provide an additional 1.20 g of the compound of formula W of lesser purity.

Step E

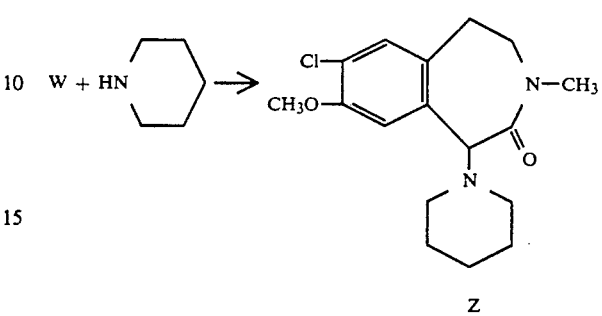

To a stirred suspension of 1.20 g of the compound of formula W above and 2.0 g of K$_2$CO$_3$ in 10 ml of DMF was added in one portion 430 mg of piperidine. The mixture was stirred at room temperature and poured into 700 ml of water with stirring. A gummy solid was filtered off. This wet solid was dissolved in 50 ml of CH$_2$Cl$_2$ and extracted with 50 ml of H$_2$O. The organic layer was separated, dried over K$_2$CO$_3$, filtered and then rotoevaporated down to dryness. The residue was recrystallized from acetonitrile (10 ml) to provide 700 mg of the compound of formula Z, m.p. 139°–141° C.

EXAMPLE 6

Step A

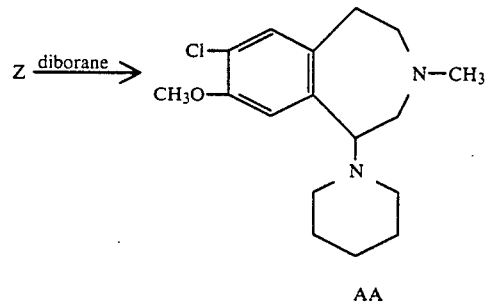

A solution of 2.95 g of the compound of formula Z, prepared as described in Preparative Example 6E, in 20 ml of THF and 40 ml of diborane in THF (1.06 M) was heated on a steam bath under reflux for 18 hours. The mixture was distilled to dryness. The residue was treated cautiously with 25 ml of 4 N HCl and then heated on a steam bath with stirring for 30 minutes. The mixture was chilled and diluted with 30 ml of water, made basic with NaOH and then extracted twice with 50 ml of ether. The ether layers were combined, dried over K$_2$CO$_3$, filtered and then rotoevaporated to dryness to provide about 2.0 g of an oily syrup which was purified through a column of 100 g of TLC grade silica gel, eluting with CH$_2$Cl$_2$/C$_2$H$_5$OH/NH$_4$OH (100/5/2). The fractions containing the desired component were combined and then rotoevaporated to dryness to provide about 540 mg of the desired material of formula AA above.

Step B

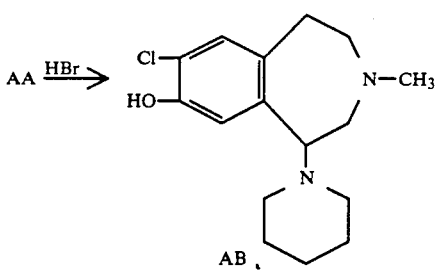

480 mg of the compound of formula AA above in 10 ml of aqueous 48% HBr was heated at 130° C. with stirring for 6½ hours. The mixture was poured into 100 ml of ice water and the pH adjusted to about 8 with NaHCO₃. The mixture was extracted twice with 40 ml of $CH_2Cl_2$. The dried combined extracts were rotoevaporated leaving 290 mg of orange colored gum-like material which was purified through 30 mg of TLC grade silica gel, eluting with $CH_2Cl_2/C_2H_5OH/NH_4OH$ (50/3/1). The residue from rotoevaporation of the fractions containing the desired component was dissolved in 30 ml of ether and allowed to evaporate slowly to about 5 ml. The solid produced was filtered off, dried at 90° C. for 5 hours to provide 75 mg of the compound of formula AB above, m.p. 155°–157° C.

By employing the Reactants listed in the first column of Table 4 below in place of piperidine in Preparative Example 6E and employing basically the same procedure as set forth in Preparative Example 6E and Example 6 above, the compounds listed in the second column of Table 4 may also be synthesized.

TABLE 4

Product

![structure with R¹]

| Reactant | R¹ = |
|---|---|
| H—N⟨  ⟩N—CH₃ | —N⟨  ⟩N—CH₃ |
| Li—C≡C—Ph* | —C≡C—Ph* |
| Li—C≡CH | —C≡CH |
| Li—⟨cyclohexyl⟩N—CH₃ | —⟨cyclohexyl⟩N—CH₃ |
| CF₃CH₂OH | —OCH₂CF₃ |

*Ph = phenyl

PREPARATIVE EXAMPLE 7

Step A

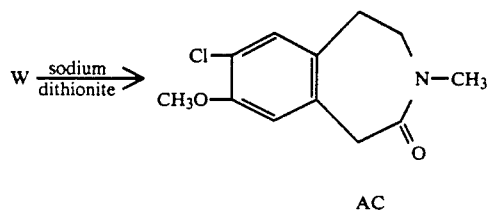

A mixture of 1.40 g of the compound of formula W, prepared as described in Preparative Example 6D, 4.0 g of NaHCO₃ and 1.75 g of sodium dithionite in 20 ml each of DMF and H₂O was stirred at room temperature for 1½ hours. 200 ml of water were added with stirring. The mixture was filtered and the solid separated was washed with water to provide about 1.09 g of solid, which was recrystallized from acetonitrile to provide a small amount of the desired compound of formula AC, m.p. 117°–118° C. The filtrate from the acetonitrile recrystallization provided 950 mg of less pure compound of formula AC.

Step B

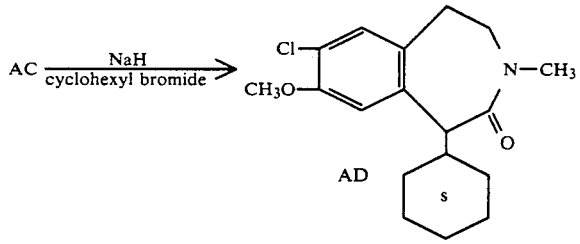

Under N₂, NaH (876 mg, 60% oil dispersion) was added to a solution of the compound of formula AC (2.5 g) in 150 ml of THF/DMF (10:1) at room temperature. A solution of cyclohexyl bromide (1.5 cc) in THF/DMF (10 cc) was added via dropping funnel to the above mixture. The mixture was heated on an oil bath at 80° C. After 2 hours the reaction was complete. Solvent was removed on a rotoevaporator at 40° C. (pump associated) and the residue was diluted rapidly with 200 cc of ice water. The resulting mixture was extracted with 200 ml of $CH_2Cl_2$ and the $CH_2Cl_2$ layer was separated and dried over MgSO₄. Rotoevaporation of the $CH_2Cl_2$ layer gave 3 g of amorphous solid which was chromatographed on Kieselgel 60G using ethyl acetate/hexane (40:60) as the eluant to give about 1.54 g of the product of formula AD.

EXAMPLE 7

Step A

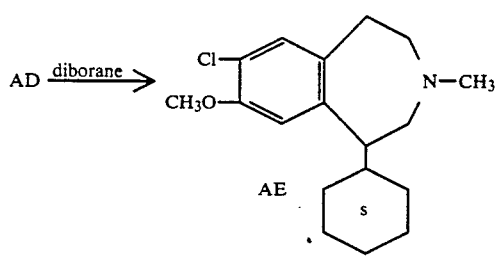

The compound of formula AD (1.53 g), prepared as described in Preparative Example 7B, dry THF (50 cc) and diborane (16 cc of a 1 M solution in THF) were refluxed for 2 hrs. The reaction mixture was cooled to room temperature and 5 cc of $H_2O$ was added carefully. Solvent was removed on a rotoevaporator at about 30° C. Ethanol (100 cc) and 25 cc of 4N HCl were added to the residue, and this mixture refluxed on a steam bath for 1½ hours. Ethanol was removed on a rotoevaporator at 50°-60° C. and the remaining aqueous portion was diluted with 100 ml of ice water. The mixture was basified with 10% NaOH solution to a pH of about 8 and extracted twice with 100 cc portions of $CH_2Cl_2$. The combined extracts were dried over $MgSO_4$, and evaporated to give 1.26 g of the compound of formula AE above as an oil.

Step B

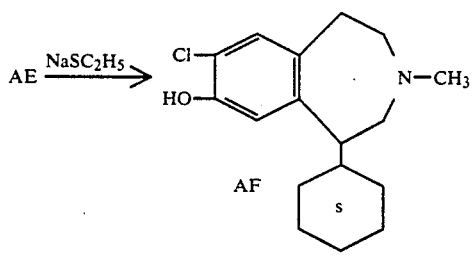

A solution of the cyclohexyl compound of formula AE above (1.2 g) in 6 ml of dimethylformamide (DMF) was added to a solution of sodium thioethoxide in 6 ml of DMF prepared from 757 mg of 60% sodium hydride in mineral oil and 1.4 ml of ethanethiol. The resulting mixture was heated at 120° C. on an oil bath for 4 hrs, cooled, diluted with 100 ml of ice-water, and washed with 50 ml of hexane 5% HCl was added to the separated aqueous layer to adjust the pH to 7.5-8. The mixture was extracted twice with 200 ml portions of $CH_2Cl_2$, and the combined extracts were dried over $MgSO_4$, filtered, and evaporated to give an oil which was dried in high vacuum. The oil partially crystallized and was recrystallized from ether-petroleum ether to give 454 mg product of the formula AF above, m.p. 144°-147° C.

By employing the reactant listed in the first column of Table 5 below in place of cyclohexyl bromide in Preparative Example 7B above and by employing basically the same basic procedures as set forth in Preparative Example 7B and Example 7, the compounds listed in the second column of Table 5 were also synthesized.

TABLE 5

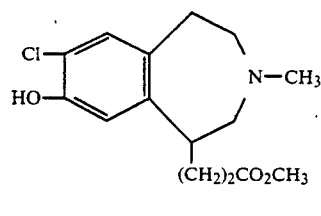

| Reactant | $R^1 =$ | m.p. |
|---|---|---|
| $Cl(CH_2)_3N(CH_3)_2$ | $-(CH_2)_3N(CH_3)_2$ | 145-160° C. (2HCl) |
| Br—⬡ | —⬡ | 170-190° C. (HCl) |

By employing the $CH_2=CH-CO_2CH_3$ in place of cyclohexyl bromide in the procedure of Preparative Example 7B and by employing basically the same procedures as described in Preparative Example 7B and Example 7, the compound AG shown below may also be prepared:

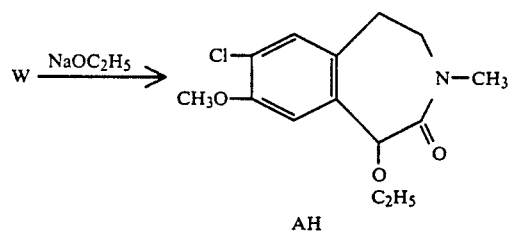

PREPARATIVE EXAMPLE 8

W $\xrightarrow{NaOC_2H_5}$

[Structure of AH shown with Cl, $CH_3O$ substituents on benzene ring fused to 7-membered ring containing $N-CH_3$, with $O-C_2H_5$ and =O groups]

AH

A solution of sodium ethoxide in 30 ml of absolute ethanol was prepared by using 253 mg of sodium, the compound of formula W (2.75 g), prepared as described in Preparative Example 6D, was added to the solution, and the reaction mixture was heated under reflux for 3 hours. The mixture was rotoevaporated down to dryness. The residue was treated with 50 ml each of $H_2O$ and $CH_2Cl_2$. The $CH_2Cl_2$ portion was dried with $MgSO_4$ and concentrated to dryness to provide 2.50 g of a solid residue which was recrystallized from 15 ml of acetonitrile to give about 780 mg of the compound of formula AH above, m.p. 106°-108° C.

EXAMPLE 8

Step A

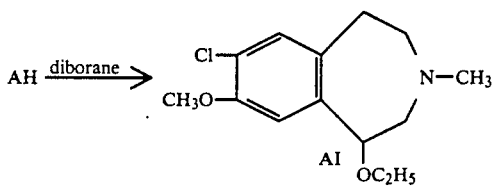

A Solution of 775 mg of the compound of formula AH, prepared as described in Preparative Example 8, in 20 ml of THF was added to 15 ml of diborane/THF (1.06 M) with stirring. The mixture was heated under reflux for 5½ hours longer and then distilled to dryness. The residue was treated with 15 ml of 4 N HCl and then heated on a steam bath with stirring for 30 minutes. The HCl mixture was diluted with 20 ml of H$_2$O, chilled and then made basic with NaOH. This mixture was extracted with 50 ml of ether. The ether was removed by rotoevaporation leaving 450 mg of an oily syrup which was a crude compound of formula AI above as confirmed by NMR.

Step B

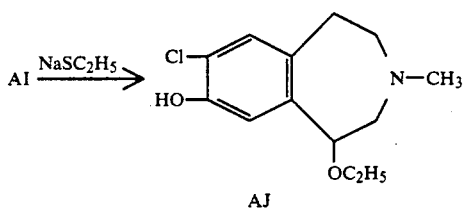

NaSC$_2$H$_5$ was prepared in DMF with 1.50 g of NaH (60% in oil) and 3.0 ml of ethanethiol in 30 ml of DMF. To 4 g of this solution was added a solution of 1.20 g of the compound of formula AI above in 2 ml of DMF. The mixture was heated on an oil bath at 130°–140° C. for 4 hours and then chilled to room temperature and poured into 150 ml of water. The pH was adjusted to about 8 with dropwise addition of acetic acid. The mixture was extracted twice with 30 ml of CH$_2$Cl$_2$. The CH$_2$Cl$_2$ layers were dried over MgSO$_4$, filtered, then rotoevaporated down to about 4–5 ml and then distilled down to dryness at 10 at 90° C. The residue was purified through a column of 50 g of TLC grade silica gel eluting with CH$_2$Cl$_2$/C$_2$H$_5$OH/NH$_4$OH (50/2.5/1). The fractions containing the desired component were combined and then rotoevaporated down to the dryness to provide about 800 mg of a viscous residue which was a crude compound of formula AJ above. The compound was converted to the hydrochloride salt in ethereal solution with a slight excess of dry HCl. The resulting salt was filtered and dried in vacuo to provide the HCl salt, m.p. 235°–236° C. (decomposes).

EXAMPLE 9

Step A

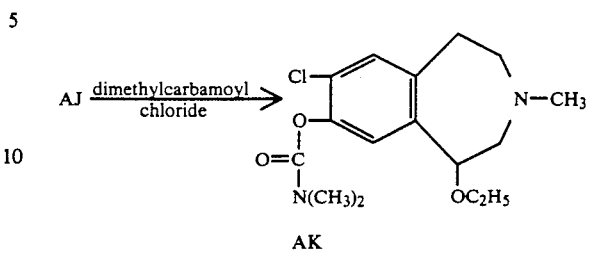

To a suspension of 0.8 g (2.7 mmole) of the hydrochloride of the compound of formula AJ, prepared as described in Example 8, in 20 ml dry dimethoxyethane was added 210 mg of NaH (60% in oil dispersion) (5.5 mmole) in portions with stirring. After evolution of gas had stopped (about 10 minutes) a solution of dimethylcarbamyl chloride (0.290 g, 0.248 ml, 2.7 mmole) in 10 ml dimethoxyethane was added and the mixture was stirred at ambient temperature overnight and then heated to 50° C. for 3 hours.

The reaction mixture was filtered (obtained 0.32 g solid, theoretical NaCl) and evaporated to near dryness. Ether and dilute NaOH were added. The phases were separated. The ether phase was washed with brine, dried over MgSO$_4$, decolorized (Darco and Florisil) and concentrated to a gum, 0.9 g, which was the compound of formula AK as confirmed by NMR.

This gummy material (0.9 g) of formula AK above from Example 9 was dissolved in ether and treated with a slight excess of etheral HCl and then filtered. The hygroscopic solid separated was redissolved immediately in about 20 ml of acetonitrile, diluted with about 100 ml ether, cooled and filtrered to provide 520 mg of the desired compound of formula AK above as the hydrochloride, m.p. 199°–202° C.

PREPARATIVE EXAMPLE 10

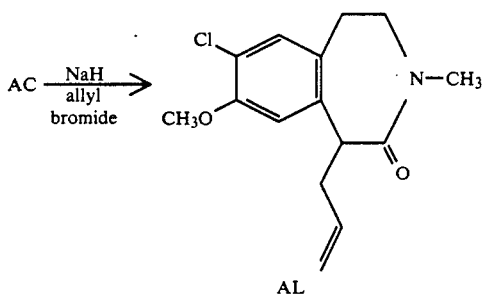

Sodium hydride (1.16 g, 60% oil dispersion) was added under nitrogen to a solution of the compound of the formula AC (3.5 g, prepared as described in Preparative Example 7A) in 35 ml of THF/DMF (10:1) at room temperature. A solution of allyl bromide (1.4 cc) in 10 ml of THF/DMF (10:1) was then added via a syringe and the mixture heated at 50° C. for 0.5 hours and then at 65° for 1 hour. The solvent was removed on a rotoevaporator at 40° C. and 200 cc of ice water rapidly added to the residue. The resulting mixture was extracted with two 150 cc portions of CH$_2$Cl$_2$ and the combined extract washed with a 50 cc portion of water and then dried over MgSO$_4$. Rotoevaporation of the CH2Cl2 extract gave 3.6 g of an oil. Recrystallization from an ethyl acetate/hexane mixture (40:60) gave 2.8 g of the product of the formula AL.

EXAMPLE 10

Step A

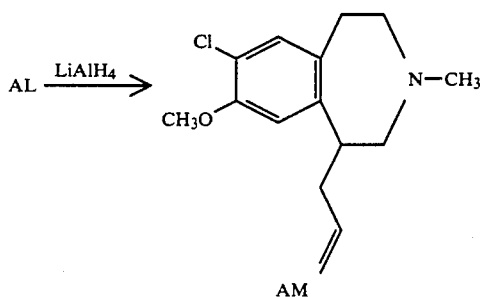

A solution of the compound AL (2.8 g), prepared as described in Preparative Example 10, in THF (30 cc) was added at room temperature to a suspension of LiAlH4 (1.1 g) in THF (50 cc). After 1 hour the reaction was complete as indicated by thin layer chromatography. To the resultant reaction mixture was added 1.1 cc of water, 1.1 cc of 15% NaOH solution and then 3.3 cc of water The precipitate was filtered off, the THF removed on a rotoevaporator and then 200 cc of water added to the residue. The mixture was then extracted with two 150 cc portions of CH2Cl2, the combined extract washed with a 75 cc portion of water and then dried over MgSO4. Rotoevaporation of the dried CH2Cl2 layer gave an oil which was chromatographed on a silica column using a 1:1 mixture of ethyl acetate and hexane as eluent to give the desired product AM as an oil (1:52 g).

Step B

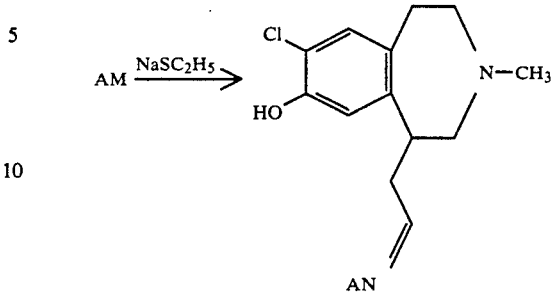

NaSC2H5 was prepared by adding batchwise 0.89 g of NaH (60% oil dispersion) to an ice-cold solution of 1.6 cc of ethanthiol in 20 cc of DMF. The reaction mixture was allowed to stand for 15 minutes and then a solution of 1.45 g of the compound of the formula AM in 30 cc of DMF was syringed into the mixture. The resulting reaction mixture was heated on an oil bath at 120° C. for 2 hours, cooled to room temperature and then 400 cc of water added. The pH of the product mixture was adjusted to 1 with N H2SO4, the mixture extracted once with 150 cc of diethyl ether and then basified with solid NaHCO3 to give a pH of 8. The mixture was extracted with two 150 cc portions of ethyl acetate and the combined extract then dried over MgSO4 and then evaporated to give an oil (840 mg). The oil was chromatographed on a silica column using 1:1 ethyl acetate:hexane as eluant to give 440 mg of product which was recrystallized from an ethyl acetate/hexane mixture to give 310 mg of the desired product AN (m.p. 141°–143° C.).

Using the procedures described in the foregoing Examples, the compounds of the general formula I set forth in the following Table 6 may be prepared.

TABLE 6

| Compound No. | $R^5$ | $R^1$ | $R^2$ | $R^3$ | m.p. °C. |
|---|---|---|---|---|---|
| 1 | HO— | =CHC6H5 | | —CH3 | 190–193 |
| 2 | HO— | —OC6H5 | —H | —CH3 | 180–182 (maleate) |
| 3 | HO— | 1-imidazolyl | —H | —CH3 | 194–195 |
| 4 | HO | OCH2C6H5 | —H | —CH3 | 153–155 |
| 5 | HO | NHC6H5 | —H | —CH3 | 193–194 |
| 6 | HO | O(CH2)2Ph | —H | —CH3 | 140–145 |
| 7 | HO | cyclopentyl | —H | —CH3 | 164–166 |
| 8 | HO | 1-pyrrolyl | —H | —CH3 | 162–163 |
| 9 | H2N | cyclohexyl | —H | —CH3 | |
| 10 | Me2NCO2 | cyclohexyl | —H | —CH3 | 112–115 |
| 11 | HO | CH2-cyclohexyl | —H | —CH3 | |
| 12 | HO | propargyl | —H | —CH3 | 150–170 (amorphous) |
| 13 | HO | allyl | —H | —CH3 | 141–143 |
| 14 | HO | —(CH2)4— | | —CH3 | 155–158 |
| 15 | t-BuCO2 | cyclohexyl | —H | —CH3 | 110–112 |
| 16 | C6H5CO2 | cyclohexyl | —H | —CH3 | >300 (HCl) |
| 17 | EtOCO2 | cyclohexyl | —H | —CH3 | |
| 18 | CH3CO2 | allyl | —H | —CH3 | 180–181 (HCl) |
| 19 | CH3CO2 | cyclohexyl | —H | —CH3 | |

TABLE 6-continued

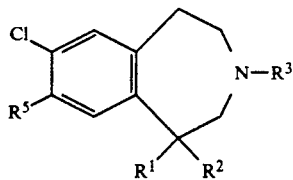

| Compound No. | R⁵ | R¹ | R² | R³ | m.p. °C. |
|---|---|---|---|---|---|
| 20 | n-PrCO₂ | allyl | —H | —CH₃ | |
| 21 | HO | 3,3-(Me)2-allyl | —H | —CH₃ | 142–144 (maleate) |
| 22 | HO | allyl | —H | —CH₃ | 183–185 |
| 23 | i-PrCO₂ | allyl | —H | —CH₃ | 232–234 (HCl) |
| 24 | HO | 2-Me allyl | —H | —CH₃ | 174–175 |
| 25 | MeOCH₂CO₂ | allyl | —H | —CH₃ | 190–192 (HCl) |
| 26 | CH₃CO₂ | 3,3-diMe-2-allyl | —H | —CH₃ | 180–183 (dec.) (HCl) |
| 27 | POM* | allyl | —H | —CH₃ | 156–159 (HCl) |
| 28 | HO | 2-butenyl (cis + trans) | —H | —CH₃ | |
| 29 | HO | cyclopropyl-methyl | —H | —CH₃ | |
| 30 | PhCO₂CH₂O | allyl | —H | —CH₃ | |
| 31 | 4-iPrPhNHCO₂ | allyl | —H | —CH₃ | |
| 32 | 4-EtOPhNHCO₂ | allyl | —H | —CH₃ | |

*POM = t-BuCOOCH₂O

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

We claim:

1. A compound having the structural formula I

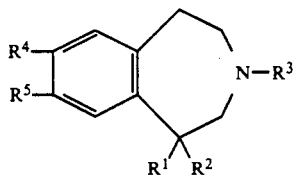

and the pharmaceutically acceptable salts thereof, wherein:

$R^1$ represents —XR⁶, —CHR⁷R⁸, cycloalkyl, cycloalkenyl, —H, -13 CN, —(CO)OR⁹, —O(CO)R⁹, —O(CO)N(R⁹)₂, —C≡CR⁹, —(CO)N(R⁹)₂,

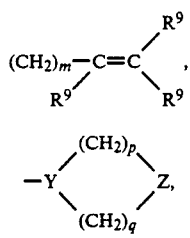

imidazolyl or pyrrolyl;

$R^2$ represents —H (provided that $R^1$ does not represent H), —OH (provided that $R^1$ does not represent —OH or —SH), or alkoxy;

in addition, $R^1$ and $R^2$ may together represent a carbonyl oxygen or a group =CH-aryl;

$R^3$ represents H, alkyl, allyl or cyclopropylmethyl;

$R^4$ represents H, halo, alkyl, haloalkyl or alkoxy;

$R^5$ represents —OR¹⁰, —N(R⁹)₂ or —OC(R⁷)₂OCOR¹³;

$R^6$ represents —H, aryl, naphthyl, aralkyl, alkyl, cycloalkyl, cycloalkenyl, haloalkyl, alkenyl, alkynyl, cycloalkylalkyl, cycloalkenylalkyl, alkoxyalkyl or —(CH₂)$_n$R¹¹;

$R^7$ represents —H or alkyl;

$R^8$ represents cycloalkyl, cylcoalkenyl, cycloalkylalkyl, cycloalkenylalkyl, aralkenyl, aralkynyl, alkenyl, alkynyl, haloalkyl, alkyxyalkyl or —(CH₂)$_n$R¹²;

each $R^9$ independently represents H, alkyl aralkyl or aryl;

$R^{10}$ represents H, —COR⁹ or —CON(R⁹)₂;

$R^{11}$ represents —(CO)OR⁹, —COR⁹, —(CO)N(R⁹)₂, —CN, —O(CO)N(R⁹)₂, —O(CO)R⁹, —N(R⁹)₂, —OR⁹ or —SR⁹, provided that R¹¹ is not —N(R⁹)₂, —OR⁹ or —SR⁹ when n is 1;

$R^{12}$ represents —(CO)OR⁹, —COR⁹, —(CO)N(R⁹)₂, —CN, —O(CO)N(R⁹)₂, —O(CO)R⁹, —N(R⁹)₂, —OR⁹ or —SR⁹;

$R^{13}$ represents alkyl, aralkyl or aryl;

X represents —O—, —S—, or —N(R⁹)—;

m represents 0 or 1;

n represents an integer of from 1 to 4;

Y represents N or CH;

Z represents CH₂ (if Y does not represent CH) or NR⁹;

p and q each independently represent integers of from 1 to 3 such that the sum of p plus q is from 1 to 5 and p and q do not both represent 1 when Y is N and Z is NR⁹;

halo represents fluoro, chloro, bromo, or iodo;

alky represents straight or branched carbon chains having 1 to 6 carbon atoms;

cycloalkyl represents a saturated carbocyclic ring containing from 3 to 8 carbon atoms;

cycloalkenyl represents a carbocyclic ring containing a carbon-carbon double bond and having 5 to 8 atoms;

alkenyl represents straight or branched carbon chains having at least one carbon-carbon double bond and containing from 2 to 6 carbon atoms;

alkynyl represents straight of branched carbon chains having at least one carbon-carbon triple bond and containing from 2 to 6 carbon atoms;

aryl represents unsubstituted phenyl or substituted phenyl;

substituted phenyl represents phenyl mono- or di-substituted by alkyl, hydroxy, alkoxy, alkylthio, halo, trifluoromethyl or combinations thereof;

carbonyl oxygen represents a group =O;

haloalkyl represents an alkyl group as defined above containing from 1 to 5 halo groups, replacing some or all of the hydrogens thereon depending on the sites of possible halogenation; and alkanediyl represents a divalent, straight or branched hydrocarbon chain having from 1 to 6 carbon atoms, the two available bonds being from the same or different carbon atoms thereof.

2. A compound according to claim 1 wherein $R^1$ represents —$XR^6$, —$CHR^7R^8$, cycloalkyl or cycloalkenyl, wherein X represents —O—, or —S—, $R^6$ represents —H, phenyl, substituted phenyl, aralkyl, alkyl, cycloalkyl, haloalkyl or alkoxyalkyl, $R^7$ represents H or alkyl preferably H and $R^8$ represents cycloalkyl, cycloalkenyl, haloalkyl, alkoxyalkyl, alkenyl or alkynyl.

3. A compound according to claim 2, wherein $R^1$ represents cyclohexyl or cyclohexenyl.

4. A compound according to claim 1, wherein $R^1$ represents

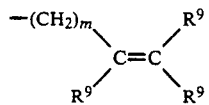

or pyrrolyl where m is 1 and $R^9$ represents hydrogen or alkyl.

5. A compound according to claim 1, said compound being selected from:

8-chloro-5-methoxy-3-methyl-2,3,4,5-tetrahydro-1H-3-benzazepine-7-ol, 8-chloro-5-ethoxy-3-methyl-2,3,4,5-tetrahydro-1H-3-benzazepine-7-ol, 8-chloro-5-ethylthio-3-methyl-2,3,4,5-tetrahydro-1H-3-benzazepine-7-ol, 8-chloro-3-methyl-5-phenoxy-2,3,4,5-tetrahydro-1H-3-benzazepin-7-ol, 8-chloro-3-methyl-5-phenylthio-2,3,4,5-tetrahydro-1H-3-benzazepin-7-ol, 7-chloro-8-dimethylcarbamoyl-1-ethoxy-methyl-2,3,4,5-tetrahydro-1H-3-benzazepine, 8-chloro-3-methyl-5-(1-piperidinyl)-2,3,4,5-tetrahydro-1H-3-benzazepine-7-ol, 8-chloro-5-cyclohexyl-3-methyl-2,3,4,5-tetrahydro-1H-3-benzazepine-7-ol, 8-chloro-5-cyclohexyloxy-3-methyl-2,3,4,5-tetrahydro-1H-3-benzazepine-7-ol, 8-chloro-5-N,N-dimethylaminopropyl-3-methyl-2,3,4,5-tetrahydro-1H-3-benzazepine-7-ol, 8-chloro-5-(2-cyclohexenyl)-3-methyl-2,3,4,5-tetrahydro-1H-3-benzazepine-7-ol, 8-chloro-5-allyl-3-methyl-2,3,4,5-tetrahydro-1H-3-benzazepine-7-ol, 8-chloro-5-(2,2,2-trifluoroethoxy)-3-methyl-2,3,4,5-tetrahydro-1H-3-benzazepine-7-ol, 8-chloro-5-benzyloxy-3-methyl-2,3,4,5-tetrahydro-1H-3-benzazepine-7-ol, 8-chloro-5-(phenethyloxy)-3-methyl-2,3,4,5-tetrahydro-1H-3-benzazepine-7-ol, 8-chloro-5-(1-pyrrolyl)-3-methyl-2,3,4,5-tetrahydro-1H-3-benzazepine-7-ol, 8-chloro-7-hydroxy-3-methyl-2,3,4,5-tetrahydrospiro[1H-3-benzazepine-5,5'-cyclopentane], 8-chloro-7-(ethoxy-formyloxy)-5-cyclohexyl-3-methyl-2,3,4,5-tetrahydro-1H-3-benzazepine, 8-chloro-7-(isopropyl-formyloxy)-5-allyl-3-methyl-2,3,4,5-tetrahydro-1H-3-benzazepine, 8-chloro-7-(methoxy-acetoxy)-5-allyl-3-methyl-2,3,4,5-tetrahydro-1H-3-benzazepine, 8-chloro-7-acetoxy-5-(3-methyl-2-butenyl)-3-methyl-2,3,4,5-tetrahydro-1H-3benzazepine, 8-chloro-7-(t-butyroxy-methoxy)-5-allyl-3-methyl-2,3,4,5-tetrahydro-1H-3-benzazepine, and the pharmaceutically acceptable salts of the foregoing.

6. A compound according to claim 1, wherein $R^2$ represents —H and $R^3$ represents —$CH_3$.

7. A compound according to claim 1, wherein $R^4$ represents halogen, and $R^5$ represents —OH, —O-CO—$R^9$ or —O—$C(R^7)_2$—$COR^{13}$, wherein $R^9$ represents alkyl, alkoxy or alkoxyalkyl, $R^7$ represents hydrogen and $R^{13}$ represents alkyl.

8. A pharmaceutical composition comprising as active ingredient a compound according to claim 1 together with a pharmaceutically acceptable carrier.

9. A method of treating psychoses in a mammal by administering to the mammal an antispychotic effective amount of a compound as claimed in claim 1.

10. A method of treating depression in a mammal by administering to the mammal an antidepressive effective amount of a compound as claimed in claim 1.

11. A method of providing for analgesia in a mammal by administering to the mammal an analgesically effective amount of a compound as claimed in claim 1.

* * * * *